United States Patent
Chen et al.

(10) Patent No.: US 11,510,673 B1
(45) Date of Patent: Nov. 29, 2022

(54) POWERED STAPLING DEVICE WITH MANUAL RETRACTION

(71) Applicant: Covidien LP, Mansfield, MA (US)

(72) Inventors: Xingrui Chen, Glastonbury, CT (US); David Chowaniec, Rocky Hill, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/329,748

(22) Filed: May 25, 2021

(51) Int. Cl.
*A61B 17/072* (2006.01)
*A61B 34/30* (2016.01)
*A61B 17/00* (2006.01)
*A61B 17/29* (2006.01)
*A61B 17/068* (2006.01)
*A61B 90/90* (2016.01)
*A61B 34/00* (2016.01)
*A61B 17/115* (2006.01)

(52) U.S. Cl.
CPC ........ *A61B 17/07207* (2013.01); *A61B 34/30* (2016.02); *A61B 17/068* (2013.01); *A61B 17/072* (2013.01); *A61B 17/115* (2013.01); *A61B 34/76* (2016.02); *A61B 90/90* (2016.02); *A61B 2017/00398* (2013.01); *A61B 2017/00407* (2013.01); *A61B 2017/07214* (2013.01); *A61B 2017/2927* (2013.01); *A61B 2017/2943* (2013.01); *A61B 2017/2946* (2013.01)

(58) Field of Classification Search
CPC ................ A61B 17/068; A61B 17/072; A61B 17/07207; A61B 17/105; A61B 17/115; A61B 2017/07214; A61B 2017/2923; A61B 2017/2927; A61B 2017/2943; A61B 2017/2946; A61B 34/30; A61B 34/74; A61B 34/76; A61B 90/90; H01M 10/425; H01M 10/48
USPC ..... 227/19, 175.1, 175.2, 176.1; 606/1, 139, 606/219
See application file for complete search history.

(56) References Cited

U.S. PATENT DOCUMENTS

| | | |
|---|---|---|
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |

(Continued)

FOREIGN PATENT DOCUMENTS

| | | |
|---|---|---|
| AU | 198654765 | 9/1986 |
| CA | 2773414 A1 | 11/2012 |

(Continued)

OTHER PUBLICATIONS

International Search Report and Written Opinion dated Sep. 6, 2022, issued in corresponding international application No. PCT/IB2022/054696, 12 pages.

(Continued)

*Primary Examiner* — Scott A Smith

(57) ABSTRACT

A powered handle assembly includes a motor assembly, a rack, a spur gear, and a manual retract mechanism. The spur gear is movable from a position engaged with the motor assembly and the rack to a positioned disengaged from the motor assembly and engaged with the rack to facilitate manual retraction of the rack.

20 Claims, 22 Drawing Sheets

(56) References Cited

U.S. PATENT DOCUMENTS

| | | |
|---|---|---|
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |

(56) References Cited

U.S. PATENT DOCUMENTS

| | | |
|---|---|---|
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,690,675 A | 11/1997 | Sawyer et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,755,338 B2 | 6/2004 | Hahnen et al. |
| 6,783,524 B2 | 8/2004 | Anderson et al. |

(56) References Cited

U.S. PATENT DOCUMENTS

| | | |
|---|---|---|
| 6,786,382 B1 | 9/2004 | Hoffman |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |

(56) References Cited

U.S. PATENT DOCUMENTS

| | | |
|---|---|---|
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,630 B2 | 11/2010 | Damadian et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |

(56) References Cited

U.S. PATENT DOCUMENTS

| | | |
|---|---|---|
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,215,532 B2 | 7/2012 | Marczyk |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |

(56) References Cited

U.S. PATENT DOCUMENTS

| | | | |
|---|---|---|---|
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,597,311 B2 | 12/2013 | Criscuolo et al. |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek et al. |

(56) References Cited

U.S. PATENT DOCUMENTS

| | | |
|---|---|---|
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,684,253 B2 | 4/2014 | Giordano et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,752,748 B2 | 6/2014 | Whitman et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,875 B2 | 7/2014 | Morgan et al. |
| 8,763,876 B2 | 7/2014 | Kostrzewski |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,631 B2 | 9/2014 | Munro, III et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,788 B2 | 9/2014 | Knodel |
| 8,851,354 B2 | 10/2014 | Swensgard et al. |
| 8,851,355 B2 | 10/2014 | Aranyi et al. |
| 8,857,693 B2 | 10/2014 | Schuckmann et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,870,050 B2 | 10/2014 | Hodgkinson |
| 8,875,971 B2 | 11/2014 | Hall et al. |
| 8,875,972 B2 | 11/2014 | Weisenburgh, II et al. |
| 8,893,949 B2 | 11/2014 | Shelton, IV et al. |
| 8,893,950 B2 | 11/2014 | Marczyk |
| 8,899,461 B2 | 12/2014 | Farascioni |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,900,616 B2 | 12/2014 | Belcheva et al. |
| 8,920,435 B2 | 12/2014 | Smith et al. |
| 8,925,782 B2 | 1/2015 | Shelton, IV |
| 8,926,598 B2 | 1/2015 | Mollere et al. |
| 8,931,681 B2 | 1/2015 | Kostrzewski |
| 8,931,682 B2 | 1/2015 | Timm et al. |
| 8,931,693 B1 | 1/2015 | Kumar et al. |
| 8,955,732 B2 | 2/2015 | Zemlok et al. |
| 8,958,429 B2 | 2/2015 | Shukla et al. |
| 8,960,517 B2 | 2/2015 | Lee |
| 8,967,443 B2 | 3/2015 | McCuen |
| 8,967,446 B2 | 3/2015 | Beardsley et al. |
| 8,973,803 B2 | 3/2015 | Hall et al. |
| 8,978,954 B2 | 3/2015 | Shelton, IV et al. |
| 8,978,956 B2 | 3/2015 | Schall et al. |
| 8,991,677 B2 | 3/2015 | Moore et al. |
| 8,991,678 B2 | 3/2015 | Wellman et al. |
| 8,998,058 B2 | 4/2015 | Moore et al. |
| 8,998,060 B2 | 4/2015 | Bruewer et al. |
| 9,005,230 B2 | 4/2015 | Yates et al. |
| 9,010,606 B2 | 4/2015 | Aranyi et al. |
| 9,010,607 B2 | 4/2015 | Kostrzewski |
| 9,010,610 B2 | 4/2015 | Hodgkinson |
| 9,016,539 B2 | 4/2015 | Kostrzewski et al. |
| 9,016,541 B2 | 4/2015 | Viola et al. |
| 9,016,542 B2 | 4/2015 | Shelton, IV et al. |
| 9,016,544 B2 | 4/2015 | Hodgkinson et al. |
| 9,016,545 B2 | 4/2015 | Aranyi et al. |
| 9,016,546 B2 | 4/2015 | Demmy et al. |
| 9,022,271 B2 | 5/2015 | Scirica |
| 9,027,817 B2 | 5/2015 | Milliman et al. |
| 9,033,203 B2 | 5/2015 | Woodard, Jr. et al. |
| 9,044,228 B2 | 6/2015 | Woodard, Jr. et al. |
| 9,044,229 B2 | 6/2015 | Scheib et al. |
| 9,050,084 B2 | 6/2015 | Schmid et al. |
| 9,055,941 B2 | 6/2015 | Schmid et al. |
| 9,060,770 B2 | 6/2015 | Shelton, IV et al. |
| 9,072,535 B2 | 7/2015 | Shelton, IV et al. |
| 9,084,601 B2 | 7/2015 | Moore et al. |
| 9,089,326 B2 | 7/2015 | Krumanaker et al. |
| 9,095,339 B2 | 8/2015 | Moore et al. |
| 9,101,359 B2 | 8/2015 | Smith et al. |
| 9,107,663 B2 | 8/2015 | Swensgard |
| 9,107,664 B2 | 8/2015 | Marczyk |
| 9,107,667 B2 | 8/2015 | Hodgkinson |
| 9,113,862 B2 | 8/2015 | Morgan et al. |
| 9,113,864 B2 | 8/2015 | Morgan et al. |
| 9,113,870 B2 | 8/2015 | Viola |
| 9,113,872 B2 | 8/2015 | Viola |
| 9,113,880 B2 | 8/2015 | Zemlok et al. |
| 9,125,649 B2 | 9/2015 | Bruewer et al. |
| 9,138,225 B2 | 9/2015 | Huang et al. |
| 9,155,537 B2 | 10/2015 | Katre et al. |
| 9,179,912 B2 | 11/2015 | Yates et al. |
| 9,192,378 B2 | 11/2015 | Aranyi et al. |
| 9,192,379 B2 | 11/2015 | Aranyi et al. |
| 9,192,384 B2 | 11/2015 | Bettuchi |
| 9,198,644 B2 | 12/2015 | Balek et al. |
| 9,198,660 B2 | 12/2015 | Hodgkinson |
| 9,198,661 B2 | 12/2015 | Swensgard |
| 9,198,662 B2 | 12/2015 | Barton et al. |

(56) References Cited

U.S. PATENT DOCUMENTS

| | | |
|---|---|---|
| 9,204,876 B2 | 12/2015 | Cappola et al. |
| 9,204,880 B2 | 12/2015 | Baxter, III et al. |
| 9,216,019 B2 | 12/2015 | Schmid et al. |
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,237,892 B2 | 1/2016 | Hodgkinson |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,272,406 B2 | 3/2016 | Aronhalt et al. |
| 9,277,919 B2 | 3/2016 | Timmer et al. |
| 9,282,962 B2 | 3/2016 | Schmid et al. |
| 9,283,054 B2 | 3/2016 | Morgan et al. |
| 9,289,209 B2 | 3/2016 | Gurumurthy et al. |
| 9,289,210 B2 | 3/2016 | Baxter, III et al. |
| 9,289,225 B2 | 3/2016 | Shelton, IV et al. |
| 9,295,464 B2 | 3/2016 | Shelton, IV et al. |
| 9,295,465 B2 | 3/2016 | Farascioni |
| 9,301,752 B2 | 4/2016 | Mandakolathur Vasudevan et al. |
| 9,301,753 B2 | 4/2016 | Aldridge et al. |
| 9,301,757 B2 | 4/2016 | Williams |
| 9,307,965 B2 | 4/2016 | Ming et al. |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,332,987 B2 | 5/2016 | Leimbach et al. |
| 9,345,477 B2 | 5/2016 | Anim et al. |
| 9,345,478 B2 | 5/2016 | Knodel |
| 9,345,481 B2 | 5/2016 | Hall et al. |
| 9,345,780 B2 | 5/2016 | Manoharan et al. |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,227 B2 | 6/2016 | Kostrzewski |
| 9,364,231 B2 | 6/2016 | Wenchell |
| 9,364,233 B2 | 6/2016 | Alexander, III et al. |
| 9,370,358 B2 | 6/2016 | Shelton, IV et al. |
| 9,370,362 B2 | 6/2016 | Petty et al. |
| 9,386,983 B2 | 7/2016 | Swensgard et al. |
| 9,386,984 B2 | 7/2016 | Aronhalt et al. |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,498,219 B2 | 11/2016 | Moore et al. |
| 9,510,827 B2 | 12/2016 | Kostrzewski |
| 9,517,065 B2 | 12/2016 | Simms et al. |
| 9,517,066 B2 | 12/2016 | Racenet et al. |
| 9,539,007 B2 | 1/2017 | Dhakad et al. |
| 9,549,735 B2 | 1/2017 | Shelton, IV et al. |
| 9,561,031 B2 | 2/2017 | Heinrich et al. |
| 9,597,077 B2 | 3/2017 | Hodgkinson |
| 9,610,080 B2 | 4/2017 | Whitfield et al. |
| 9,913,646 B2 | 3/2018 | Shelton, IV |
| 9,936,954 B2 | 4/2018 | Shelton, IV et al. |
| 9,987,099 B2 | 6/2018 | Chen et al. |
| 10,004,497 B2 | 6/2018 | Overmyer et al. |
| 10,004,505 B2 | 6/2018 | Moore et al. |
| 10,045,782 B2 | 8/2018 | Murthy Aravalli |
| 10,064,622 B2 | 9/2018 | Murthy Aravalli |
| 10,076,325 B2 | 9/2018 | Huang et al. |
| 10,135,242 B2 | 11/2018 | Baber et al. |
| 10,143,474 B2 | 12/2018 | Bucciaglia et al. |
| 10,172,615 B2 | 1/2019 | Marczyk et al. |
| 10,206,677 B2 | 2/2019 | Harris et al. |
| 10,265,066 B2 | 4/2019 | Measamer et al. |
| 10,265,074 B2 | 4/2019 | Shelton, IV et al. |
| 10,271,841 B2 | 4/2019 | Overmyer et al. |
| 10,327,776 B2 | 6/2019 | Harris et al. |
| 10,349,941 B2 | 7/2019 | Marczyk et al. |
| 10,390,828 B2 | 8/2019 | Vendely et al. |
| 10,405,857 B2 | 9/2019 | Shelton |
| 10,463,368 B2 | 11/2019 | Kostrzewski |
| 10,478,182 B2 | 11/2019 | Taylor |
| 10,478,183 B2 | 11/2019 | Hess et al. |
| 10,548,599 B2 | 2/2020 | Marczyk et al. |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0006429 A1 | 1/2005 | Wales et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0308907 A1 | 12/2009 | Nalagatla et al. |
| 2010/0012703 A1 | 1/2010 | Calabrese et al. |
| 2010/0051669 A1 | 3/2010 | Milliman |
| 2010/0069942 A1 | 3/2010 | Shelton, IV |
| 2010/0089970 A1 | 4/2010 | Smith et al. |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |

(56) References Cited

U.S. PATENT DOCUMENTS

| | | |
|---|---|---|
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2011/0006101 A1 | 1/2011 | Hall et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0087276 A1 | 4/2011 | Bedi et al. |
| 2011/0101069 A1 | 5/2011 | Bombard et al. |
| 2011/0114702 A1 | 5/2011 | Farascioni |
| 2011/0121049 A1 | 5/2011 | Malinouskas et al. |
| 2011/0147433 A1 | 6/2011 | Shelton, IV et al. |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0278343 A1 | 11/2011 | Knodel et al. |
| 2011/0290856 A1 | 12/2011 | Shelton, IV et al. |
| 2012/0053406 A1 | 3/2012 | Conlon et al. |
| 2012/0061446 A1 | 3/2012 | Knodel et al. |
| 2012/0074200 A1 | 3/2012 | Schmid et al. |
| 2012/0080478 A1 | 4/2012 | Morgan et al. |
| 2012/0080495 A1 | 4/2012 | Holcomb et al. |
| 2012/0080498 A1 | 4/2012 | Shelton, IV et al. |
| 2012/0091183 A1 | 4/2012 | Manoux et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0234895 A1 | 9/2012 | O'Connor et al. |
| 2012/0234897 A1 | 9/2012 | Shelton, IV et al. |
| 2012/0241492 A1 | 9/2012 | Shelton, IV et al. |
| 2012/0241493 A1 | 9/2012 | Baxter, III et al. |
| 2012/0241504 A1 | 9/2012 | Soltz et al. |
| 2012/0248169 A1 | 10/2012 | Widenhouse et al. |
| 2012/0286021 A1 | 11/2012 | Kostrzewski |
| 2012/0286022 A1 | 11/2012 | Olson et al. |
| 2012/0298722 A1 | 11/2012 | Hess et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037595 A1 | 2/2013 | Gupta et al. |
| 2013/0041406 A1 | 2/2013 | Bear et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0075447 A1 | 3/2013 | Weisenburgh, II et al. |
| 2013/0092717 A1 | 4/2013 | Marczyk et al. |
| 2013/0098964 A1 | 4/2013 | Smith et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | Racenet et al. |
| 2013/0112730 A1 | 5/2013 | Whitman et al. |
| 2013/0119109 A1 | 5/2013 | Farascioni et al. |
| 2013/0146641 A1 | 6/2013 | Shelton, IV et al. |
| 2013/0146642 A1 | 6/2013 | Shelton, IV et al. |
| 2013/0153636 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0175316 A1 | 7/2013 | Thompson et al. |
| 2013/0193188 A1 | 8/2013 | Shelton, IV et al. |
| 2013/0256380 A1 | 10/2013 | Schmid et al. |
| 2013/0277410 A1 | 10/2013 | Fernandez et al. |
| 2013/0334280 A1 | 12/2013 | Krehel et al. |
| 2014/0014704 A1 | 1/2014 | Onukuri et al. |
| 2014/0014707 A1 | 1/2014 | Onukuri et al. |
| 2014/0021242 A1 | 1/2014 | Hodgkinson et al. |
| 2014/0048580 A1 | 2/2014 | Merchant et al. |
| 2014/0061280 A1 | 3/2014 | Ingmanson et al. |
| 2014/0076955 A1 | 3/2014 | Lorenz |
| 2014/0151431 A1 | 6/2014 | Hodgkinson et al. |
| 2014/0166720 A1 | 6/2014 | Chowaniec et al. |
| 2014/0166721 A1 | 6/2014 | Stevenson et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175146 A1 | 6/2014 | Knodel |
| 2014/0175150 A1 | 6/2014 | Shelton, IV et al. |
| 2014/0203062 A1 | 7/2014 | Viola |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239043 A1 | 8/2014 | Simms et al. |
| 2014/0239044 A1 | 8/2014 | Hoffman |
| 2014/0239047 A1 | 8/2014 | Hodgkinson et al. |
| 2014/0246471 A1 | 9/2014 | Jaworek et al. |
| 2014/0246472 A1 | 9/2014 | Kimsey et al. |
| 2014/0246475 A1 | 9/2014 | Hall et al. |
| 2014/0246478 A1 | 9/2014 | Baber et al. |
| 2014/0252062 A1 | 9/2014 | Mozdzierz |
| 2014/0252064 A1 | 9/2014 | Mozdzierz et al. |
| 2014/0252065 A1 | 9/2014 | Hessler et al. |
| 2014/0263539 A1 | 9/2014 | Leimbach et al. |
| 2014/0263540 A1 | 9/2014 | Covach et al. |
| 2014/0263541 A1 | 9/2014 | Leimbach et al. |
| 2014/0263542 A1 | 9/2014 | Leimbach et al. |
| 2014/0263544 A1 | 9/2014 | Ranucci et al. |
| 2014/0263546 A1 | 9/2014 | Aranyi |
| 2014/0263550 A1 | 9/2014 | Aranyi et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263557 A1 | 9/2014 | Schaller |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263570 A1 | 9/2014 | Hopkins et al. |
| 2014/0284371 A1 | 9/2014 | Morgan et al. |
| 2014/0291379 A1 | 10/2014 | Schellin et al. |
| 2014/0291380 A1 | 10/2014 | Weaner et al. |
| 2014/0291383 A1 | 10/2014 | Spivey et al. |
| 2014/0303668 A1 | 10/2014 | Nicholas et al. |
| 2014/0309665 A1 | 10/2014 | Parihar et al. |
| 2014/0332578 A1 | 11/2014 | Fernandez et al. |
| 2014/0339286 A1 | 11/2014 | Motooka et al. |
| 2014/0353358 A1 | 12/2014 | Shelton, IV et al. |
| 2014/0367445 A1 | 12/2014 | Ingmanson et al. |
| 2014/0367446 A1 | 12/2014 | Ingmanson et al. |
| 2015/0048143 A1 | 2/2015 | Scheib et al. |
| 2015/0053737 A1* | 2/2015 | Leimbach .............. H01M 10/48 227/175.1 |
| 2015/0053738 A1* | 2/2015 | Morgan .................... H02J 7/00 227/175.1 |
| 2015/0053740 A1 | 2/2015 | Shelton, IV |
| 2015/0053742 A1 | 2/2015 | Shelton, IV et al. |
| 2015/0053744 A1 | 2/2015 | Swayze et al. |
| 2015/0054753 A1* | 2/2015 | Morgan .............. H01M 10/425 345/173 |
| 2015/0060517 A1 | 3/2015 | Williams |
| 2015/0076205 A1 | 3/2015 | Zergiebel |
| 2015/0076209 A1* | 3/2015 | Shelton, IV ........... A61B 34/10 227/176.1 |
| 2015/0076211 A1 | 3/2015 | Irka et al. |
| 2015/0080912 A1 | 3/2015 | Sapre |

(56) References Cited

U.S. PATENT DOCUMENTS

| | | |
|---|---|---|
| 2015/0133996 A1 | 5/2015 | Shelton, IV et al. |
| 2015/0134076 A1 | 5/2015 | Shelton, IV et al. |
| 2015/0150556 A1 | 6/2015 | McCuen |
| 2015/0157321 A1 | 6/2015 | Zergiebel et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173748 A1 | 6/2015 | Marczyk et al. |
| 2015/0173749 A1 | 6/2015 | Shelton, IV et al. |
| 2015/0173750 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0209040 A1 | 7/2015 | Whitman et al. |
| 2015/0250474 A1 | 9/2015 | Abbott et al. |
| 2015/0272557 A1 | 10/2015 | Overmyer et al. |
| 2015/0297222 A1 | 10/2015 | Huitema et al. |
| 2015/0297225 A1 | 10/2015 | Huitema et al. |
| 2015/0316431 A1 | 11/2015 | Collins et al. |
| 2015/0351765 A1 | 12/2015 | Valentine et al. |
| 2015/0359534 A1 | 12/2015 | Gibbons, Jr. |
| 2015/0366560 A1 | 12/2015 | Chen et al. |
| 2015/0374371 A1 | 12/2015 | Richard et al. |
| 2015/0374372 A1 | 12/2015 | Zergiebel et al. |
| 2015/0374376 A1 | 12/2015 | Shelton, IV |
| 2016/0030040 A1 | 2/2016 | Calderoni et al. |
| 2016/0051259 A1 | 2/2016 | Hopkins et al. |
| 2016/0058443 A1 | 3/2016 | Yates et al. |
| 2016/0066907 A1 | 3/2016 | Cheney et al. |
| 2016/0067074 A1 | 3/2016 | Thompson et al. |
| 2016/0089137 A1 | 3/2016 | Hess et al. |
| 2016/0095585 A1 | 4/2016 | Zergiebel et al. |
| 2016/0100835 A1 | 4/2016 | Linder et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2016/0120542 A1 | 5/2016 | Westling et al. |
| 2016/0166249 A1 | 6/2016 | Knodel |
| 2016/0166253 A1 | 6/2016 | Knodel |
| 2016/0199064 A1 | 7/2016 | Shelton, IV et al. |
| 2016/0199084 A1 | 7/2016 | Takei |
| 2016/0206336 A1 | 7/2016 | Frushour |
| 2016/0235494 A1 | 8/2016 | Shelton, IV et al. |
| 2016/0242773 A1 | 8/2016 | Sadowski et al. |
| 2016/0242774 A1 | 8/2016 | Ebner |
| 2016/0242779 A1 | 8/2016 | Aranyi et al. |
| 2016/0249915 A1 | 9/2016 | Beckman et al. |
| 2016/0249916 A1 | 9/2016 | Shelton, IV et al. |
| 2016/0249918 A1 | 9/2016 | Shelton, IV et al. |
| 2016/0249927 A1 | 9/2016 | Beckman et al. |
| 2016/0249929 A1 | 9/2016 | Cappola et al. |
| 2016/0249945 A1 | 9/2016 | Shelton, IV et al. |
| 2016/0256071 A1 | 9/2016 | Shelton, IV et al. |
| 2016/0256152 A1 | 9/2016 | Kostrzewski |
| 2016/0256154 A1 | 9/2016 | Shelton, IV et al. |
| 2016/0256160 A1 | 9/2016 | Shelton, IV et al. |
| 2016/0256161 A1 | 9/2016 | Overmyer et al. |
| 2016/0256162 A1 | 9/2016 | Shelton, IV et al. |
| 2016/0256163 A1 | 9/2016 | Shelton, IV et al. |
| 2016/0256184 A1 | 9/2016 | Shelton, IV et al. |
| 2016/0256185 A1 | 9/2016 | Shelton, IV et al. |
| 2016/0256187 A1 | 9/2016 | Shelton, IV et al. |
| 2016/0262750 A1 | 9/2016 | Hausen et al. |
| 2016/0270783 A1 | 9/2016 | Yigit et al. |
| 2016/0270788 A1 | 9/2016 | Czernik |
| 2016/0278764 A1 | 9/2016 | Shelton, IV et al. |
| 2016/0278765 A1 | 9/2016 | Shelton, IV et al. |
| 2016/0278771 A1 | 9/2016 | Shelton, IV et al. |
| 2016/0278774 A1 | 9/2016 | Shelton, IV et al. |
| 2016/0278775 A1 | 9/2016 | Shelton, IV et al. |
| 2016/0278777 A1 | 9/2016 | Shelton, IV et al. |
| 2016/0278848 A1 | 9/2016 | Boudreaux et al. |
| 2016/0287250 A1 | 10/2016 | Shelton, IV et al. |
| 2016/0287251 A1 | 10/2016 | Shelton, IV et al. |
| 2016/0296216 A1 | 10/2016 | Nicholas et al. |
| 2016/0302791 A1 | 10/2016 | Schmitt |
| 2016/0310134 A1 | 10/2016 | Contini et al. |
| 2016/0324514 A1 | 11/2016 | Srinivas et al. |
| 2016/0324518 A1 | 11/2016 | Nicholas et al. |
| 2016/0338703 A1 | 11/2016 | Scirica et al. |
| 2016/0354176 A1 | 12/2016 | Schmitt |
| 2016/0374678 A1 | 12/2016 | Becerra et al. |
| 2017/0000483 A1 | 1/2017 | Motai et al. |
| 2017/0020525 A1 | 1/2017 | Shah |
| 2017/0245854 A1 | 8/2017 | Zemlok et al. |
| 2019/0183594 A1 | 6/2019 | Shelton, IV et al. |

FOREIGN PATENT DOCUMENTS

| | | |
|---|---|---|
| CA | 2884962 A1 | 11/2015 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1952769 A2 | 8/2008 |
| EP | 2090253 A2 | 8/2009 |
| EP | 2090254 A1 | 8/2009 |
| EP | 2583630 A2 | 4/2013 |
| EP | 2586382 A2 | 5/2013 |
| EP | 2606834 A2 | 6/2013 |
| EP | 2907456 A1 | 8/2015 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |

(56) References Cited

FOREIGN PATENT DOCUMENTS

| | | | |
|---|---|---|---|
| GB | 2070499 | A | 9/1981 |
| GB | 2141066 | A | 12/1984 |
| GB | 2165559 | A | 4/1986 |
| JP | 51149985 | | 12/1976 |
| JP | 2001087272 | | 4/2001 |
| SU | 659146 | A1 | 4/1979 |
| SU | 728848 | A1 | 4/1980 |
| SU | 980703 | A1 | 12/1982 |
| SU | 990220 | A1 | 1/1983 |
| WO | 2008302247 | | 7/1983 |
| WO | 8910094 | A1 | 11/1989 |
| WO | 9210976 | A1 | 7/1992 |
| WO | 9308754 | A1 | 5/1993 |
| WO | 9314706 | A1 | 8/1993 |
| WO | 2004032760 | A2 | 4/2004 |
| WO | 2009071070 | A2 | 6/2009 |
| WO | 20150191887 | A1 | 12/2015 |

OTHER PUBLICATIONS

International Search Report and Written Opinion dated Sep. 6, 2022, issued in corresponding international application No. PCT/IB2022/054686, 13 pages.

\* cited by examiner

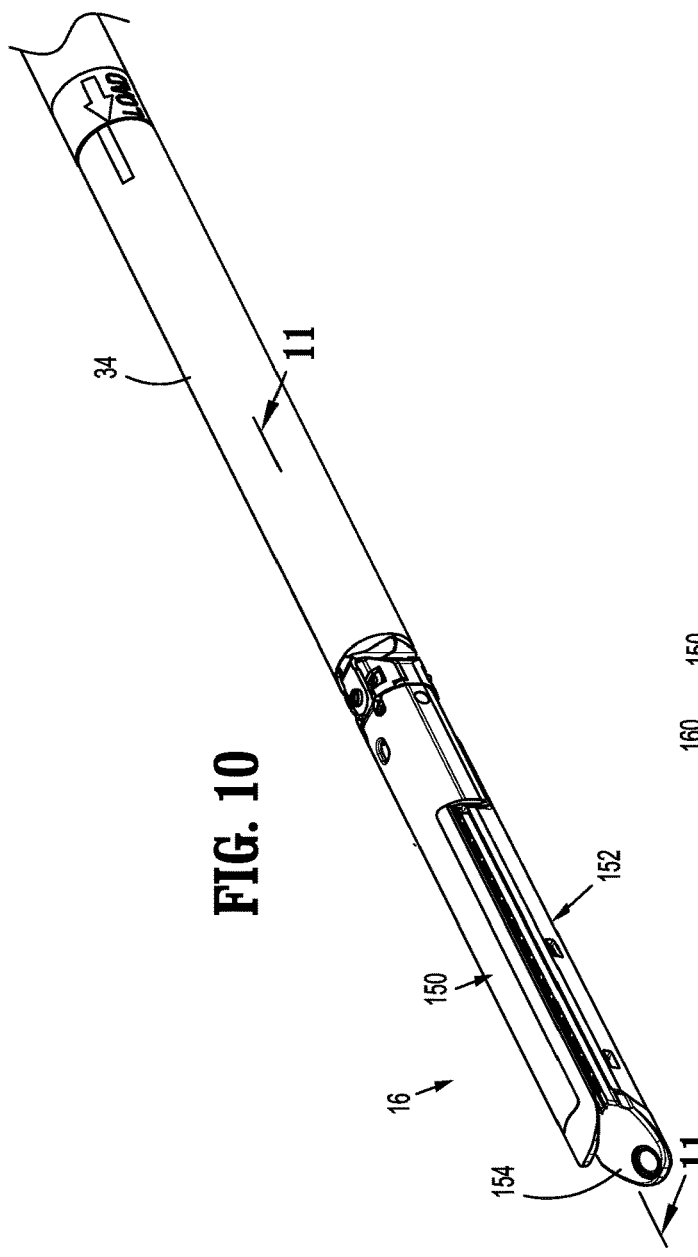
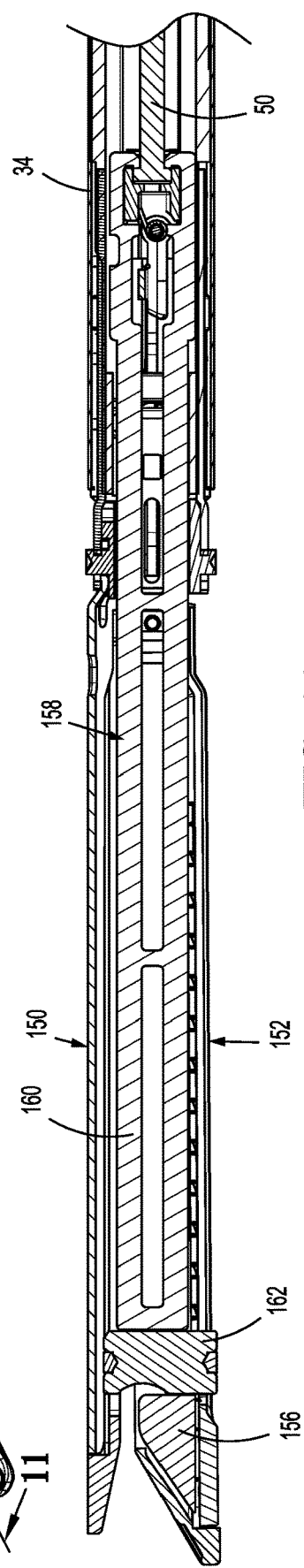
FIG. 10
FIG. 11

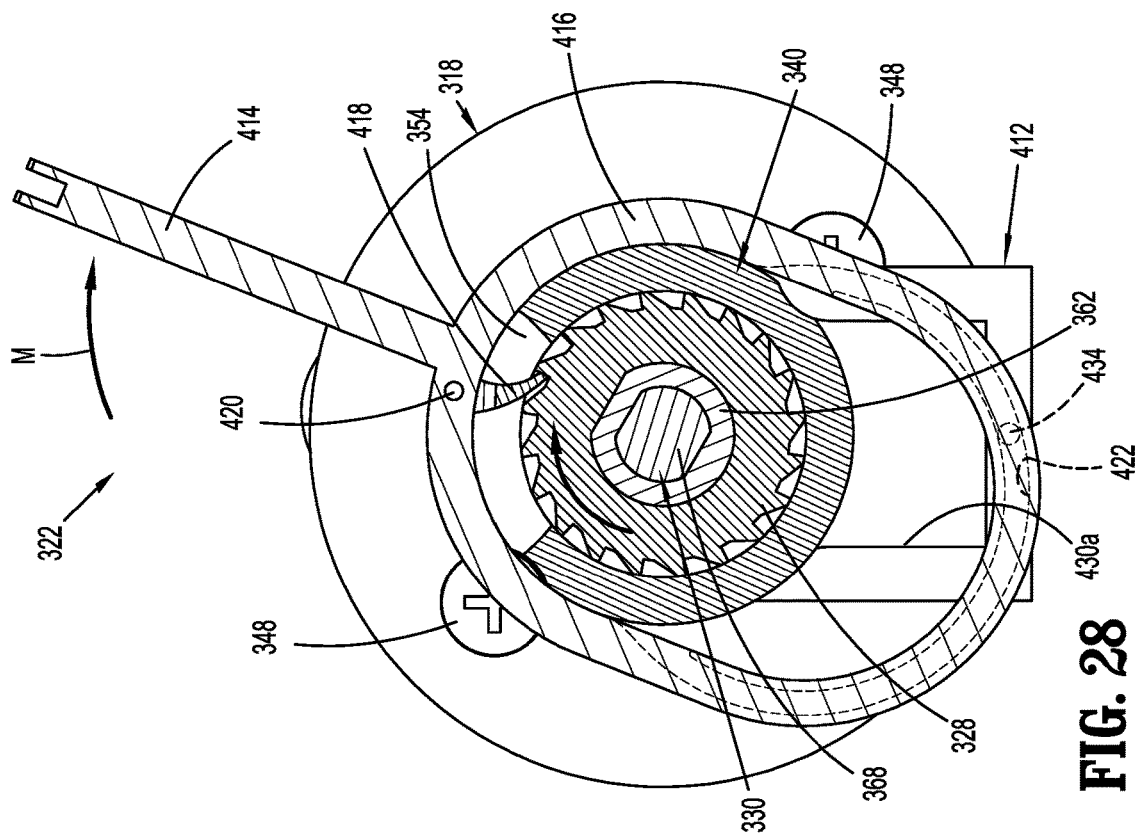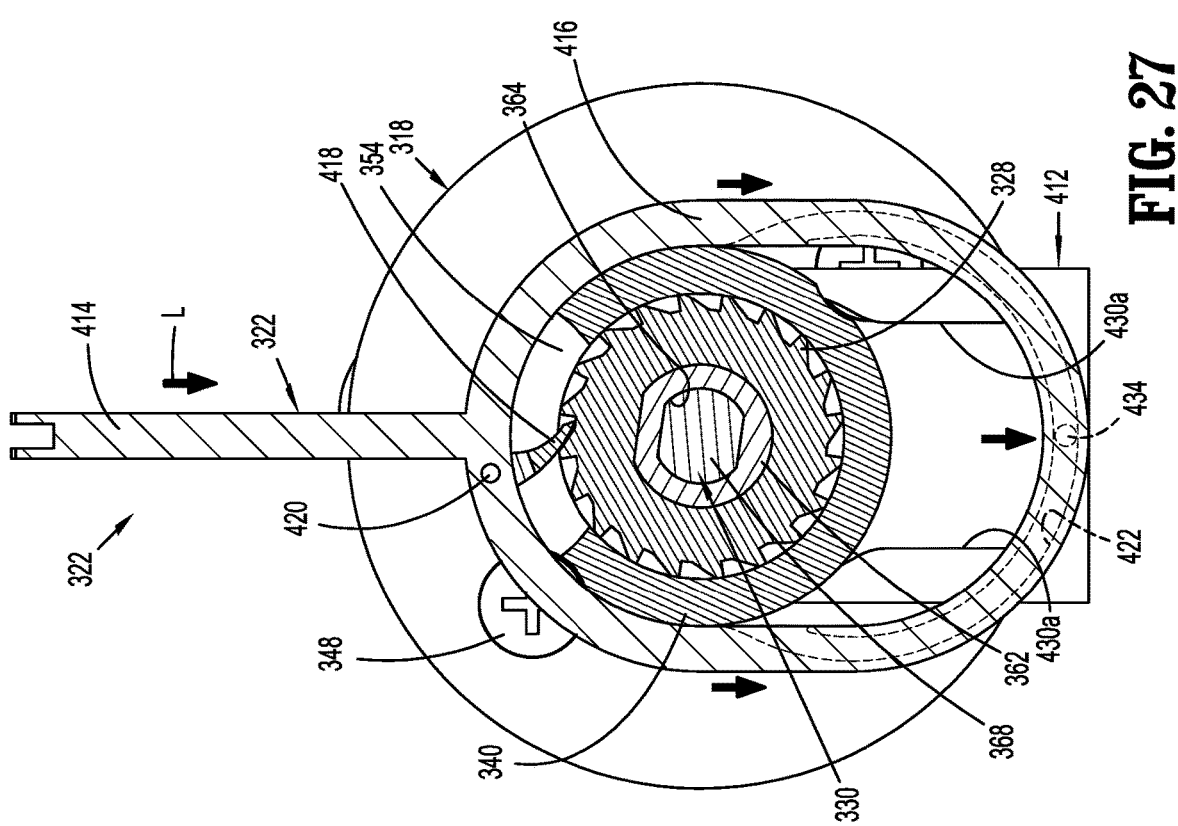

POWERED STAPLING DEVICE WITH MANUAL RETRACTION

FIELD

This disclosure is directed to surgical devices and, more particularly, to powered surgical stapling devices.

BACKGROUND

Various types of surgical devices used to endoscopically treat tissue are known in the art, and are commonly used, for example, for closure of tissue or organs in transection, resection, and anastomoses procedures, for occlusion of organs in thoracic and abdominal procedures, and for electrosurgically fusing or sealing tissue.

One example of such a surgical device is a surgical stapling device. Typically, surgical stapling devices include a tool assembly having an anvil assembly and a cartridge assembly, and a drive assembly. Typically, the drive assembly includes a flexible drive beam and a clamp member that is supported on a distal end of the drive beam. The drive assembly is movable to advance the clamp member through the tool assembly to approximate the cartridge and anvil assemblies and to advance an actuation sled through the cartridge assembly to eject staples from the cartridge assembly.

Surgical stapling devices can be manually actuated devices in which a clinician squeezes a trigger to actuate the stapling device, or powered stapling devices in which a clinician activates a motor within the stapling device to actuate the stapling device. Although powered stapling devices require less force to operate, difficulties may arise when the device loses power or components of the device break. In such instances, the device can remain clamped about tissue preventing removal of the device from a patient.

A continuing need exists in the art for a powered stapling device that includes a drive assembly that can be manually retracted when power is lost or when the device is not operational.

SUMMARY

A surgical device includes a powered handle assembly having a motor assembly, a rack, a spur gear, and a manual retract mechanism. The spur gear is movable from a position engaged with the motor assembly and the rack to a positioned disengaged from the motor assembly and engaged with the rack to facilitate manual retraction of the rack.

One aspect of the disclosure is directed to a powered handle assembly for a surgical device that includes a housing, a gear casing, a motor assembly, a rack, a rotating shaft, and a spur gear. The housing defines a cavity. The gear casing is supported within the cavity of the housing and defines a longitudinal channel, a first cavity, and a second cavity that communicate with each other. The motor assembly includes an output shaft and a drive gear that is secured to the output shaft. The motor assembly is secured to the gear casing, and the drive gear is positioned within the second cavity of the gear casing. The rack is received within the longitudinal channel of the gear casing and is movable between retracted and advanced positions. The rotating shaft extends through the first cavity of the gear casing. The spur gear is coupled to the rotating shaft and is received within the first cavity of the gear casing. The spur gear is movable within the first cavity from a first position in which the spur gear is engaged with the drive gear and the rack to a second position in which the spur gear is disengaged from the drive gear and engaged with the rack.

Other aspects of the disclosure are directed to a powered handle assembly for a surgical device that includes a housing, a motor assembly, a rack, a rotating shaft, and a spur gear. The housing defines a cavity. The motor assembly is supported within housing and includes an output shaft and a drive gear that is secured to the output shaft. The rack is supported within the housing and is movable longitudinally between retracted and advanced positions. The rotating shaft is supported within the housing. The spur gear is coupled to the rotating shaft and received within the housing such that the spur gear is movable from a first position in which the spur gear is engaged with the drive gear and the rack to a second position in which the spur gear is disengaged from the drive gear and engaged with the rack.

In aspects of the disclosure, the crank lever is coupled to the rotating shaft and is movable to move the spur gear from the first position to the second position.

In some aspects of the disclosure, a biasing member is engaged with the spur gear and urges the spur gear towards the first position.

In certain aspects of the disclosure, the rotating shaft includes a first portion and a second portion, wherein the first portion is rotatably fixed to the spur gear and the second portion receives the crank lever.

In aspects of the disclosure, the housing defines an opening and includes a removable cover that is positioned over the opening such that the crank lever is accessible through the opening.

In some aspects of the disclosure, the crank lever is movable along the second portion of the rotating shaft from a first position in which the rotating shaft can rotate independently of the crank lever to a second position in which the crank lever is rotatably fixed to the rotating shaft.

In certain aspects of the disclosure, the crank lever includes a hub that defines a through bore having a rectangular portion and the second portion of the rotating shaft includes a rectangular portion that is received within the rectangular portion of the through bore when the crank lever is in its second position.

In aspects of the disclosure, the handle assembly includes first and second C-clips, and the second portion of the rotating shaft defines spaced annular grooves that receive the first and second C-clips, respectively.

In some aspects of the disclosure, the spur gear is received about the second portion of the rotating shaft atop the first C-clip within the first cavity of the gear casing and the second C-clip is positioned externally of the first cavity of the gear casing to secure the rotating shaft to the gear casing.

Another aspect of the disclosure is directed to surgical stapling device that includes a powered handle assembly, an adapter assembly, and a tool assembly. The powered handle assembly includes a housing, a gear casing, a motor assembly, a rack, a rotating shaft, and a spur gear. The housing defines a cavity. The gear casing is supported within the cavity of the housing and defines a longitudinal channel, a first cavity, and a second cavity that communicate with each other. The motor assembly includes an output shaft and a drive gear secured to the output shaft. The motor assembly is secured to the gear casing, and the drive gear is positioned within the second cavity of the gear casing. The rack is received within the longitudinal channel of the gear casing and is movable between retracted and advanced positions. The rotating shaft extends through the first cavity of the gear casing. The spur gear is coupled to the rotating shaft and is received within the first cavity of the gear casing. The spur gear is movable within the first cavity from a first position in which the spur gear is engaged with the drive gear and the rack to a second position in which the spur gear is disengaged from the drive gear and engaged with the rack. The adapter assembly has a proximal portion coupled to the handle assembly and a distal portion. The adapter assembly includes a firing rod that is coupled to the rack and is movable between retracted and advanced positions in response to movement of the rack between its retracted and advanced positions. The tool assembly is supported on the distal portion of the adapter assembly.

In aspects of the disclosure, the tool assembly includes an anvil and a cartridge assembly that are movable between open and clamped positions.

In some aspects of the disclosure, the stapling device includes a drive assembly that is coupled to the firing rod and includes a working end having an I-beam configuration.

In certain aspects of the disclosure, the working end of the drive assembly is movable in relation to the anvil and the cartridge assembly in response to movement of the firing rod between its retracted and advanced positions.

Other aspects of the disclosure are directed to a powered handle assembly for a surgical device that includes a housing, a gear casing, a motor assembly, a drive screw, a drive nut, a connecting rod, and a spur gear. The housing defines a cavity. The gear casing is supported within the cavity of the housing and defines a channel. The motor assembly includes an output shaft and a drive gear secured to the output shaft. The motor assembly is secured to the gear casing, and the drive gear is positioned within the cavity of the gear casing. The drive screw is supported within the housing and is rotatable in response to activation of the motor assembly. The drive nut is supported on and movable along the drive screw between retracted and advanced positions. The connecting rod is coupled to the drive nut. The spur gear is movable within the channel of the gear casing from a first position in which the spur gear is engaged with the output shaft and the drive screw to a second position in which the spur gear is disengaged from the output shaft and engaged with the drive screw.

Other aspects of the disclosure are directed to a powered handle assembly for a surgical device that includes a housing, a motor assembly, a drive screw, a drive nut, a connecting rod, a spur gear, a locking clip, and a pawl assembly. The housing defines a cavity. The motor assembly includes an output shaft and a drive gear secured to the output shaft. The motor assembly is positioned within the housing and the drive gear is positioned within the cavity of the gear casing. The drive screw is supported within the housing and is rotatable in response to activation of the motor assembly. The drive nut is supported on and movable along the drive screw between retracted and advanced positions. The connecting rod is coupled to the drive nut. The spur gear is movable within the channel of the gear casing from a first position in which the spur gear is engaged with the output shaft and the drive screw to a second position in which the spur gear is disengaged from the output shaft and engaged with the drive screw. The locking clip is movable from a first position retaining the spur gear in its first position to a second position allowing movement of the spur gear from its first position to its second position. The pawl assembly includes an annular body portion and a ratcheting pawl coupled to the body portion.

In aspects of the disclosure, the handle assembly includes a biasing member that is positioned to urge the spur gear to the second position.

In some aspects of the disclosure, the handle assembly includes a locking clip that is movable from a first position retaining the spur gear in its first position to a second position allowing movement of the spur gear from its first position to its second position.

In certain aspects of the disclosure, the handle assembly includes a pawl assembly that includes a body portion and a ratcheting pawl coupled to the body portion.

In aspects of the disclosure, the gear casing defines a window and the body portion of the pawl assembly is positioned about the gear casing adjacent the window such that the pawl assembly is movable from a first position in which the ratcheting pawl is spaced from the spur gear to a second position in which the ratcheting pawl is engaged with the spur gear.

In some aspects of the disclosure, the connecting rod includes a proximal portion coupled to the drive nut and a distal portion coupled to a coupling member.

In certain aspects of the disclosure, the coupling member is adapted to engage a firing rod of the surgical device.

In aspects of the disclosure, the pawl assembly is coupled to the locking clip such that movement of the pawl assembly from its first position to its second position moves the locking clip from its first position to its second position.

In some aspects of the disclosure, the gear casing defines spaced openings, and the locking clip includes legs that are received within the openings.

Still other aspects of the disclosure are directed to a stapling device including a powered handle assembly, an adapter assembly, and a tool assembly. The powered handle assembly includes a housing, a gear casing, a motor assembly, a drive screw, a drive nut, a connecting rod, and a spur gear. the housing defines a cavity. The gear casing is supported within the cavity of the housing and defines a channel. The motor assembly includes an output shaft and a drive gear secured to the output shaft. The motor assembly is secured to the gear casing, and the drive gear is positioned within the cavity of the gear casing. The drive screw is supported within the housing and is rotatable in response to activation of the motor assembly. The drive nut is supported on and movable along the drive screw between retracted and advanced positions. The connecting rod is coupled to the drive nut. The spur gear is movable within the channel of the gear casing from a first position in which the spur gear is engaged with the output shaft and the drive screw to a second position in which the spur gear is disengaged from the output shaft and engaged with the drive screw. The adapter assembly has a proximal portion coupled to the handle assembly and a distal portion. The adapter assembly includes a firing rod that is coupled to the drive nut and is movable between retracted and advanced positions in response to movement of the drive nut between its retracted and advanced positions. The tool assembly is supported on the distal portion of the adapter assembly.

Other features of the disclosure will be appreciated from the following description.

BRIEF DESCRIPTION OF THE DRAWINGS

Various embodiments of the disclosed staple cartridge are described herein below with reference to the drawings, wherein:

FIG. 10 is a side perspective view of a reload assembly of the stapling device shown in FIG. 1 in the clamped and fired position;

FIG. 11 is a cross-sectional view taken along section line 11-11 of FIG. 10;

FIG. 27 is a cross-sectional view taken along section line 27-27 of FIG. 26 illustrating the manual retract mechanism as the manual retract mechanism is operated to move the locking clip from the locked position to the unlocked position; and FIG. 28 is a cross-sectional view taken along section line 27-27 of FIG. 26 illustrating the manual retract mechanism as the manual retract mechanism is operated to retract the drive assembly.

DETAILED DESCRIPTION

Figure 1:
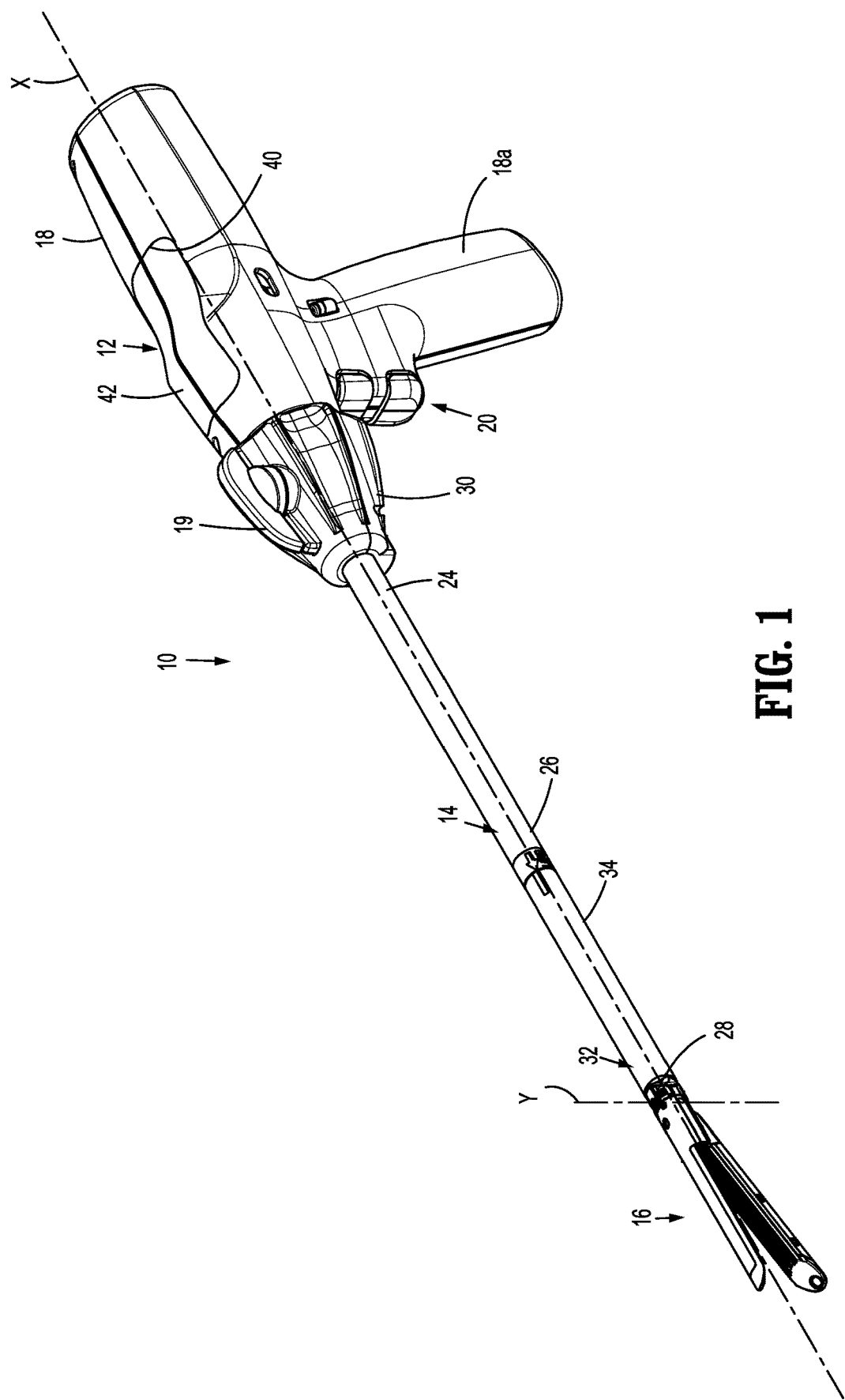
FIG. 1 is a side perspective view of a first version of a stapling device according to aspects of the disclosure with the stapling device in a non-articulated, unclamped position.

The disclosed surgical device will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "endoscopic" is used generally to refer to endoscopic, laparoscopic, arthroscopic, and/or any other procedure conducted through a small diameter incision or cannula. Further, the term "clinician" is used generally to refer to medical personnel including doctors, nurses, surgeons, and support personnel.

This disclosure is directed to a surgical device that includes a powered handle assembly having a motor assembly, a rack, a spur gear, and a manual retract mechanism. The spur gear is movable from a position engaged with the motor assembly and the rack to a positioned disengaged from the motor assembly and engaged with the rack to facilitate manual retraction of the rack.

Figure 2:
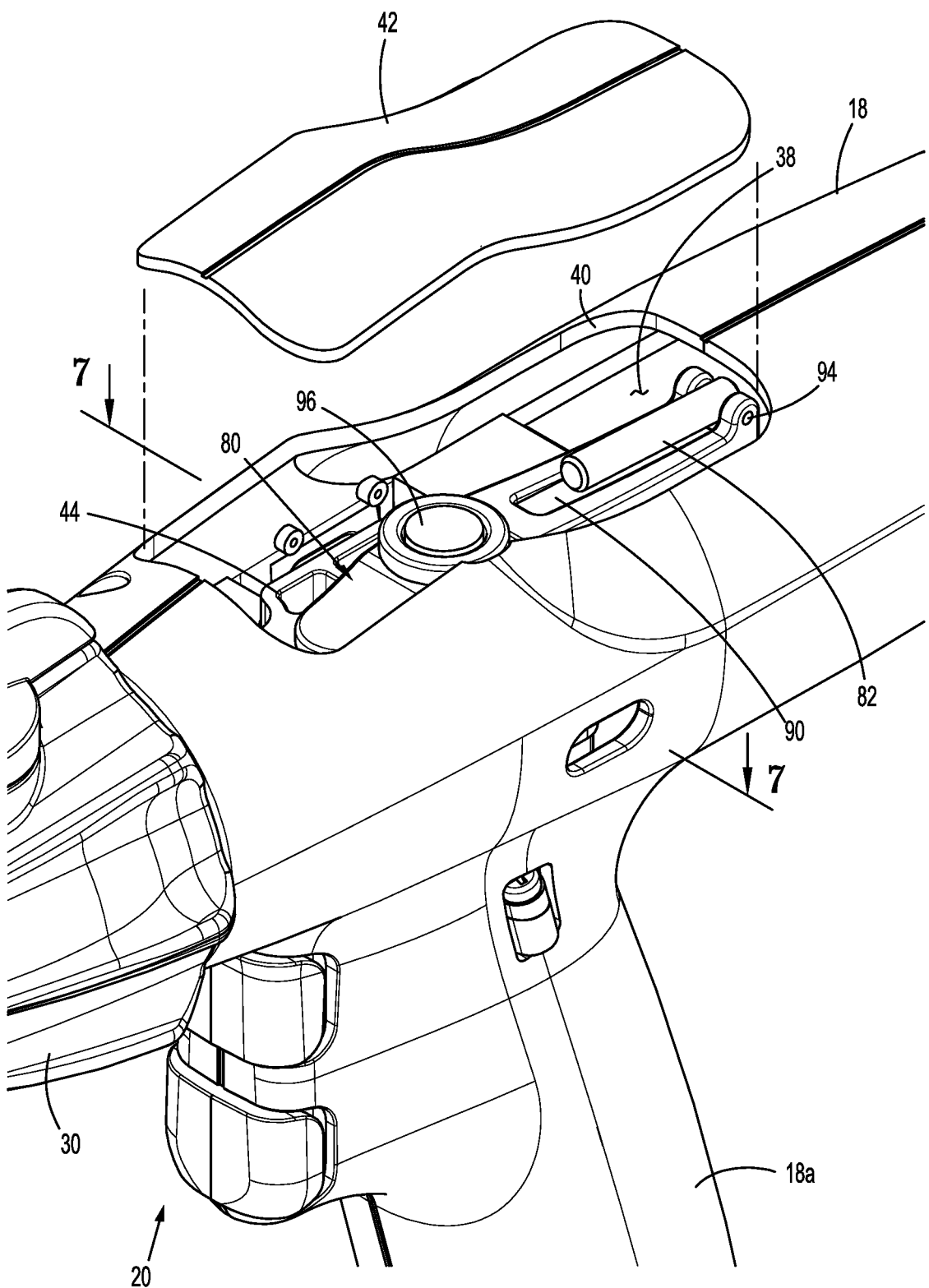
FIG. 2 is a side cutaway view of a handle assembly of the stapling device shown in FIG. 1 with a cover of the handle assembly removed.

FIGS. 1 and 2 illustrate a surgical device shown generally as stapling device 10 which includes a handle assembly 12, an elongate body or adapter assembly 14, and a tool assembly 16. The handle assembly 12 includes a housing 18 that forms a stationary handle portion 18a, and articulation lever 19, and actuation buttons 20. The adapter assembly 14 defines a longitudinal axis "X" and includes a proximal portion 24 that is coupled to the handle assembly 12, and a distal portion 26 that supports the tool assembly 16. The tool assembly 16 is secured to the distal portion 26 of the adapter assembly 14 by a pivot member 28 that defines an axis "Y" that is transverse to the longitudinal axis "X". The articulation lever 19 is operatively coupled to the tool assembly 16 via an articulation linkage (not shown) such that manipulation of the articulation lever 19 causes articulation of the tool assembly 16 about the axis "Y" between an articulated position in which the tool assembly 16 is aligned with the longitudinal axis "Y" and non-articulated positions in which a longitudinal axis of the tool assembly and the longitudinal axis "X" define acute angles in response to manipulation of the articulation lever 19. The adapter assembly 14 is supported within a rotation knob 30 that is rotatably coupled to a distal portion of the handle assembly 12. The rotation knob 30 is manually rotatable about the longitudinal axis "X" to rotate the adapter assembly 14 and the tool assembly 16 about the longitudinal axis "X". The actuation buttons 20 control operation of the different functions of the stapling device 10 including clamping and firing of the stapling device 10.

In aspects of the disclosure, the tool assembly 16 forms part of a reload assembly 32 that includes a proximal body portion 34 and the tool assembly 16. The proximal body portion 34 of the reload assembly 32 forms an extension of the adapter assembly 14 and includes a proximal end that is adapted to be releasably coupled to a distal end of the adapter assembly 14 and a distal end that supports the tool assembly 16 for articulation. In aspects of the disclosure, the tool assembly 16 can be fixedly coupled to a distal portion of the adapter assembly 14.

In aspects of the disclosure, the housing 18 of the handle assembly 12 is formed from half-sections that are coupled together such as by welding of with screws to define a cavity 38 that receives internal components of the handle assembly 12 which are described in further detail below. The housing 18 defines an upper opening 40 that provides access to the internal components of the handle assembly 12. The upper opening 40 is enclosed by a cover 42 that is removably supported within the upper opening 40.

Figure 3:
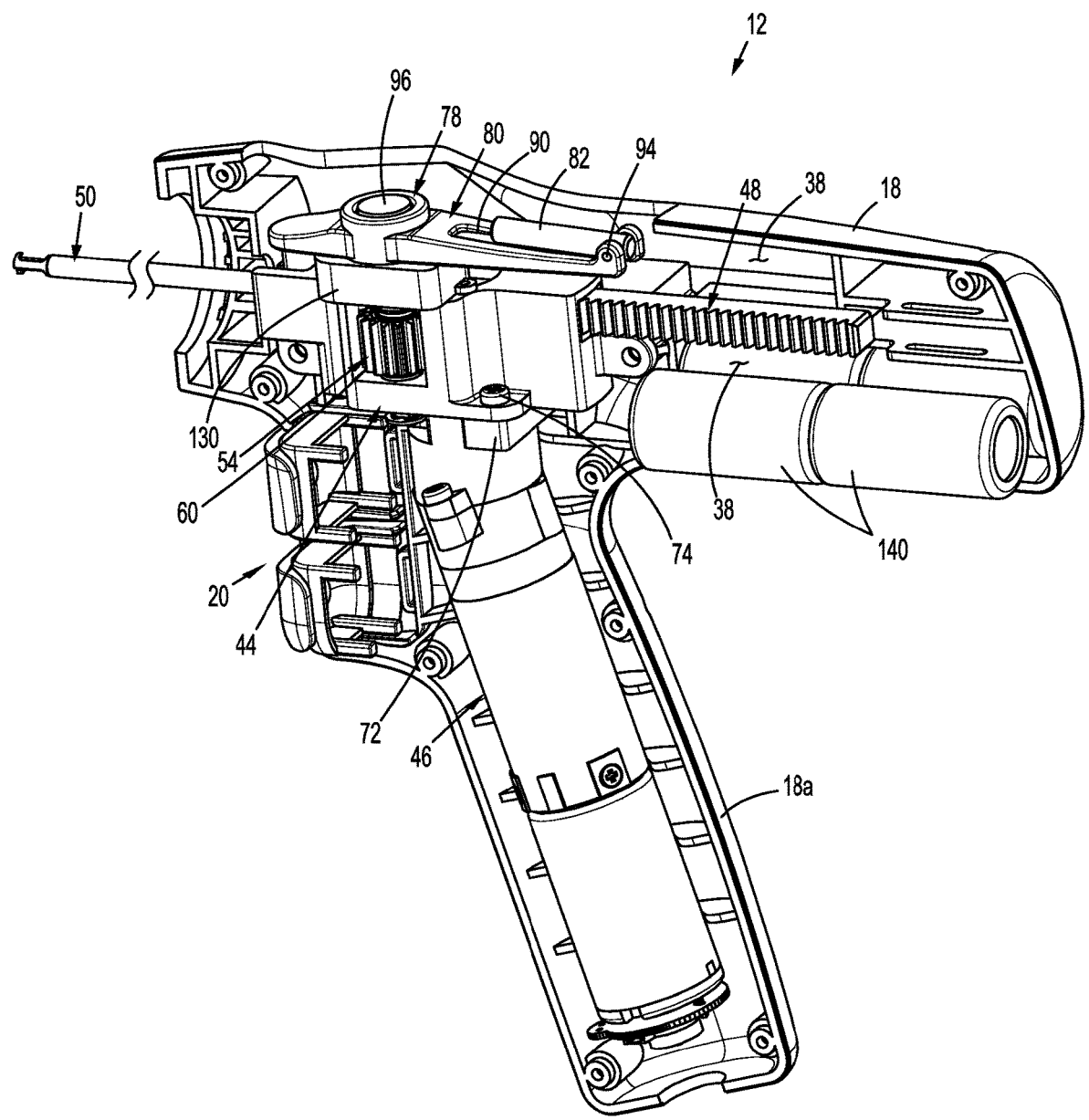
FIG. 3 is a side perspective view of the handle assembly of the stapling device shown in FIG. 1 with a housing half-section removed.
Figure 4:
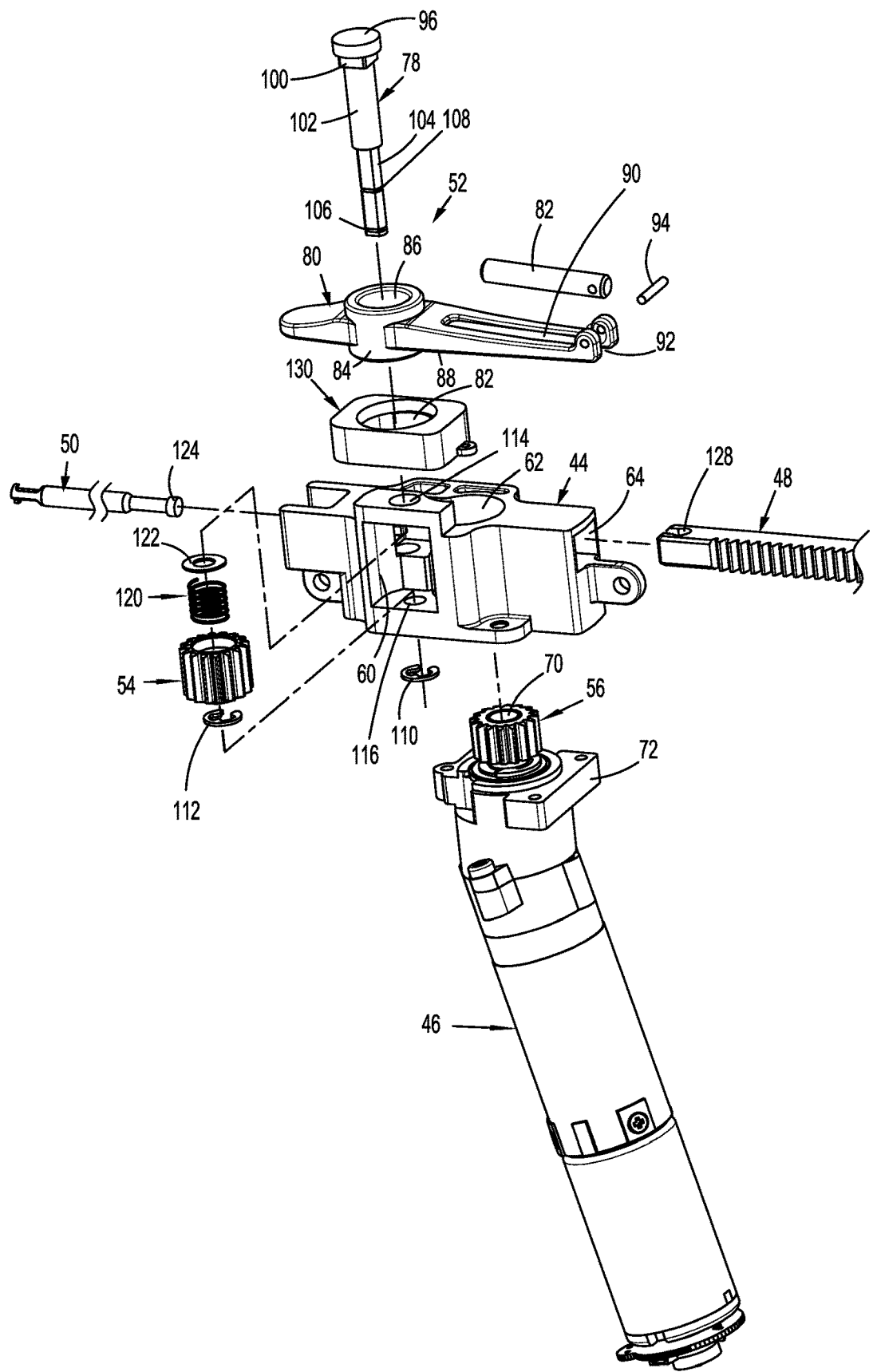
FIG. 4 is an exploded side perspective view of internal components of the handle assembly shown in FIG. 3.

FIGS. 3 and 4 illustrate the internal components of the handle assembly 12 which include a gear casing 44, a motor assembly 46, a rack 48, a firing rod 50, a manual retract mechanism 52 and intermediate spur gear 54, and a drive gear 56. The gear casing 44 is secured within the cavity 38 of the housing 18 using screws or the like and defines a first cavity 60 and a second cavity 62 that intersect with each other and a longitudinally extending channel 64. The first cavity 60 of the gear casing 44 receives the drive gear 56 and the second cavity 62 of the gear casing 44 receives the intermediate spur gear 54. The drive gear 56 and the intermediate spur gear each include gear teeth that mesh such that rotation of the drive gear 56 within the first cavity 60 causes corresponding rotation of the intermediate spur gear 54 within the second cavity 62. The rack 48 is received within the channel 64 of the gear casing 44 and includes gear teeth that mesh with the gear teeth of the intermediate spur gear 54. When the drive gear 56 is rotated to rotate the intermediate spur gear 54, engagement between the intermediate spur gear 56 and the rack 48 causes the rack 48 to move longitudinally through the channel 64 in the gear casing 44.

The motor assembly 46 includes an output shaft 70 (FIG. 4) that is secured to the drive gear 56 and can be activated via the actuation buttons 20 (FIG. 1) to rotate the drive gear 56. In aspects of the disclosure, the motor assembly 46 is positioned within a portion of the cavity 38 of the housing 18 defined by the stationary handle portion 18a. The motor assembly 46 includes a mounting bracket 72 that is secured to the gear casing 44 with screws 74 such that the drive gear 56 is received within the second cavity 62 of the gear casing 44.

Figure 5:
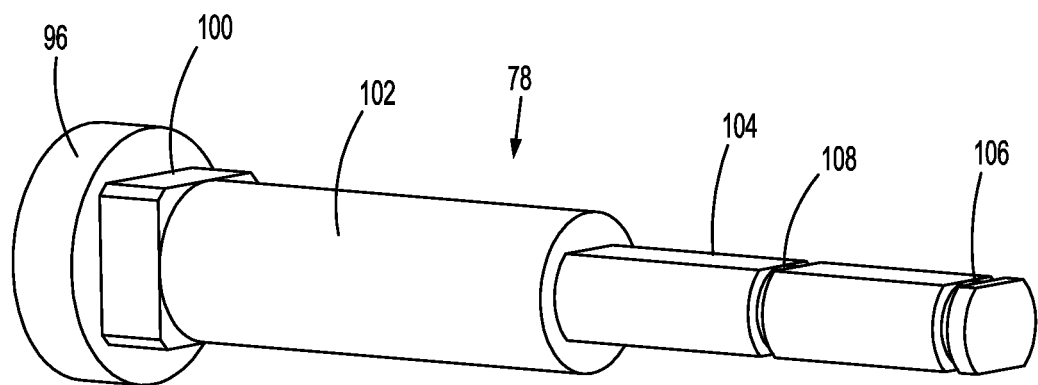
FIG. 5 is a side perspective view of a rotating shaft of the handle assembly shown in FIG. 3.
Figure 6:
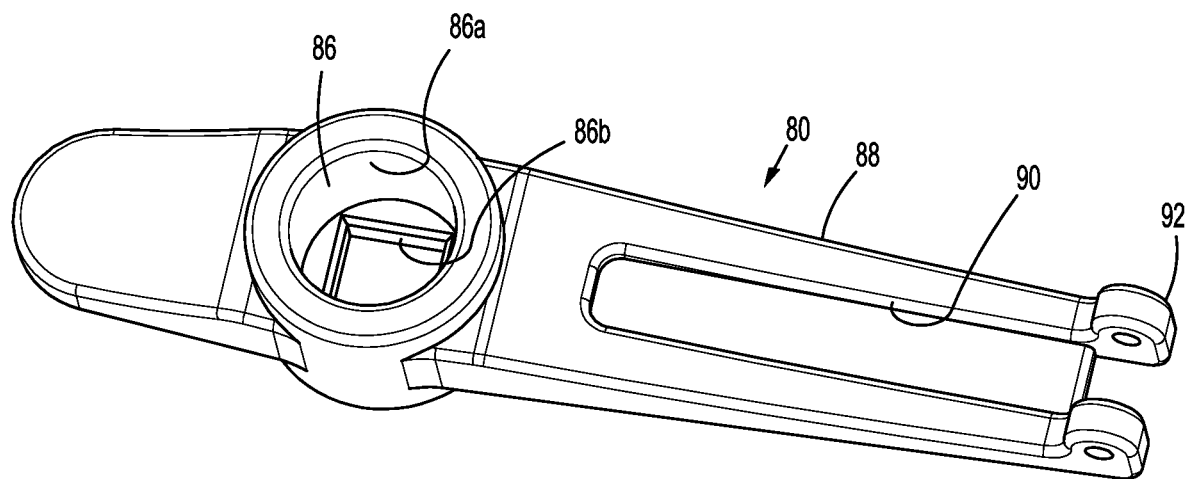
FIG. 6 is a perspective view of a crank lever of the handle assembly shown in FIG. 3.

FIGS. 4-6 illustrate the manual retract mechanism 52 which includes a rotating shaft 78, a crank lever 80, and a grip member 82. The crank lever 80 includes a central hub portion 84 that defines a through bore 86 that receives the rotating shaft 78. The through bore 86 includes a cylindrical portion 86a and a rectangular portion 86b. The crank lever 80 also includes a lever portion 88 that defines a slot 90 and forms a clevis 92. The grip member 82 is supported within the clevis 92 by a pivot member 94 and is pivotable between a first position located within the slot 90 and a second position extending orthogonally from the lever portion 88.

The rotating shaft 78 includes a head portion 96 and a shaft portion 98 that extends downwardly from the head portion 96 as viewed in FIG. 4 through the through bore 86 in the crank lever 80. The shaft portion 98 includes a first rectangular portion 100, a cylindrical portion 102, and a second rectangular portion 104. The second rectangular portion 104 includes spaced annular grooves 106 and 108 that receive C-clips 110 and 112, respectively. The intermediate spur gear 54 is received about the second rectangular portion 104 of the rotating shaft 78 atop the C-clip 112 within the first cavity 60 of the gear casing 44. The C-clip 112 is positioned externally of the first cavity 60 and secures the rotating shaft 78 to the gear casing 44. Although the rotating shaft 78 is shown to have first and second rectangular portions, it is envisioned that other shaft configurations are envisioned.

The gear casing 44 defines first and second openings 114 and 116 that communicate with upper and lower ends of the first cavity 60 of the gear casing 44. The cylindrical portion 102 of the rotating shaft 78 is received within the first opening 114 of the gear casing 44 and the second rectangular portion 104 of the rotating shaft 78 extends through the second opening 116 of the gear casing 44. The C-clip 110 is secured to the lower end of the second rectangular portion 104 of the rotating shaft 78 adjacent a lower surface of the gear casing 44 and the C-clip 112 is secured to the second rectangular portion 104 of the rotating shaft 78 within the first cavity 60 of the gear casing 44. The C-clips 110 and 112 secure the intermediate spur gear 54 to the rotating shaft 78 and secure the rotating shaft 78 to the gear casing 44. The second rectangular portion 104 of the rotating shaft 78 is received within a rectangular bore in the intermediate spur gear 54 to rotatably fix the intermediate spur gear 54 to the rotating shaft 78.

The intermediate spur gear 54 is received within the first cavity 60 of the gear casing 44 and is movable within the first cavity between a first or lower position and a second or upper position. In the lower position (FIG. 8), the teeth of the intermediate spur gear 54 simultaneously engage the teeth of the rack 48 and the teeth of the drive gear 56. In the upper position, the teeth of the intermediate spur gear 54 engage only the teeth of the rack 48.

The manual retract mechanism 52 includes a biasing member 120 that is positioned between an upper surface of the intermediate spur gear 54 and the inner surface of the gear casing 44. The biasing member 120 urges the intermediate spur gear 54 towards its lower position in which the intermediate spur gear 54 is engaged with both the drive gear 56 and the rack 48. In some aspects of the disclosure, a washer 122 is positioned between an upper surface of the biasing member 120 and the inner surface of the gear casing 44. In some aspects of the disclosure, the biasing member 120 includes a coil spring. It is envisioned that other types of biasing members could be incorporated into the stapling device 10 (FIG. 1).

The rack 44 includes a distal portion that is coupled to the firing rod 50, In aspects of the disclosure, the proximal portion of the firing rod 50 is formed with a head 124 that has a diameter that is larger than a body of the firing rod 50 and the distal portion of the rack 48 defines a slot 128. The head 124 of the firing rod 50 is received within the slot 128 of the rack 48 to couple the firing rod 50 to the rack 48 such that longitudinal movement of the rack 48 causes longitudinal movement of the firing rod 50. The coupling of the head 124 and the slot 128 allows the firing rod 50 to rotate in relation to the rack 48.

In some aspects of the disclosure, the manual retract mechanism 52 includes a base member 130 that defines a circular bore 132. The base member 130 is secured to an upper surface of the gear casing 44 and the hub portion 84 of the crank lever 80 is aligned within the circular bore 132. The crank lever 80 is movable from a lowered position to a raised position. In the lowered position, the hub portion 84 of the crank lever 80 is received within the circular bore 132 and in the raised position, the hub portion 84 of the crank lever 80 is positioned above the circular bore 132 of the base member 130.

The head 96 of the rotating shaft 78 of the manual retract mechanism 52 is received within the bore 86 of the crank lever 80. When the crank lever 80 is in its lowered position, the cylindrical portion 102 of the rotating shaft 78 is received within the rectangular portion 86b (FIG. 6) of the through bore 86 of the crank lever 80. In this position, the rotating shaft 78 can rotate within the through bore 86 of the crank lever 80 without causing rotation of the crank lever 80. When the crank lever 80 is moved to its raised position, the first rectangular portion 100 of the rotating shaft 78 is received within the rectangular portion 86b of the through bore 86 of the crank lever 80, In this position, rotation of the crank lever 80 causes corresponding rotation of the rotating shaft 78, and thus, rotation of the intermediate spur gear 54. The head 96 of the rotating shaft 78 has a diameter that is larger than the width of the rectangular portion 86b of the through bore 86 of the crank lever 80. Thus, movement of the crank lever 80 to its raised position causes the rotating shaft 78 to its upper position in which the teeth of the intermediate spur gear 54 are only engaged with the teeth of the rack 48.

The handle assembly 12 (FIG. 1) also includes one or more batteries 140 which are received within the cavity 38 of the housing 18 of the handle assembly 12. The batteries 140 provide power to the motor assembly 46 via the actuation switches and control circuitry (not shown), e.g., a printed circuit board and one or more controllers, within the handle assembly 12 to control firing of the stapling device 10.

Figure 7:
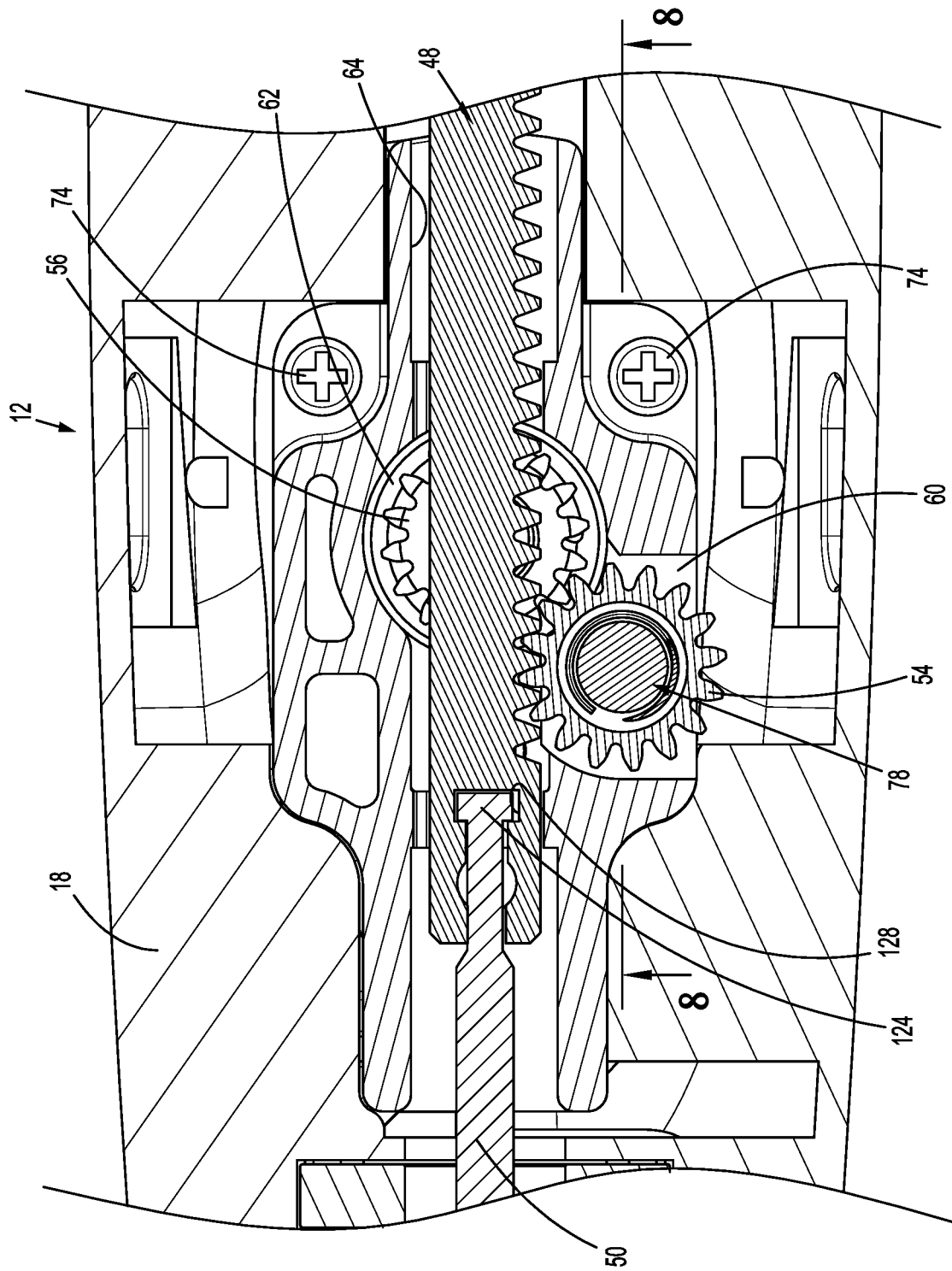
FIG. 7 is a cross-sectional view taken along section line 7-7 of FIG. 2.
Figure 8:
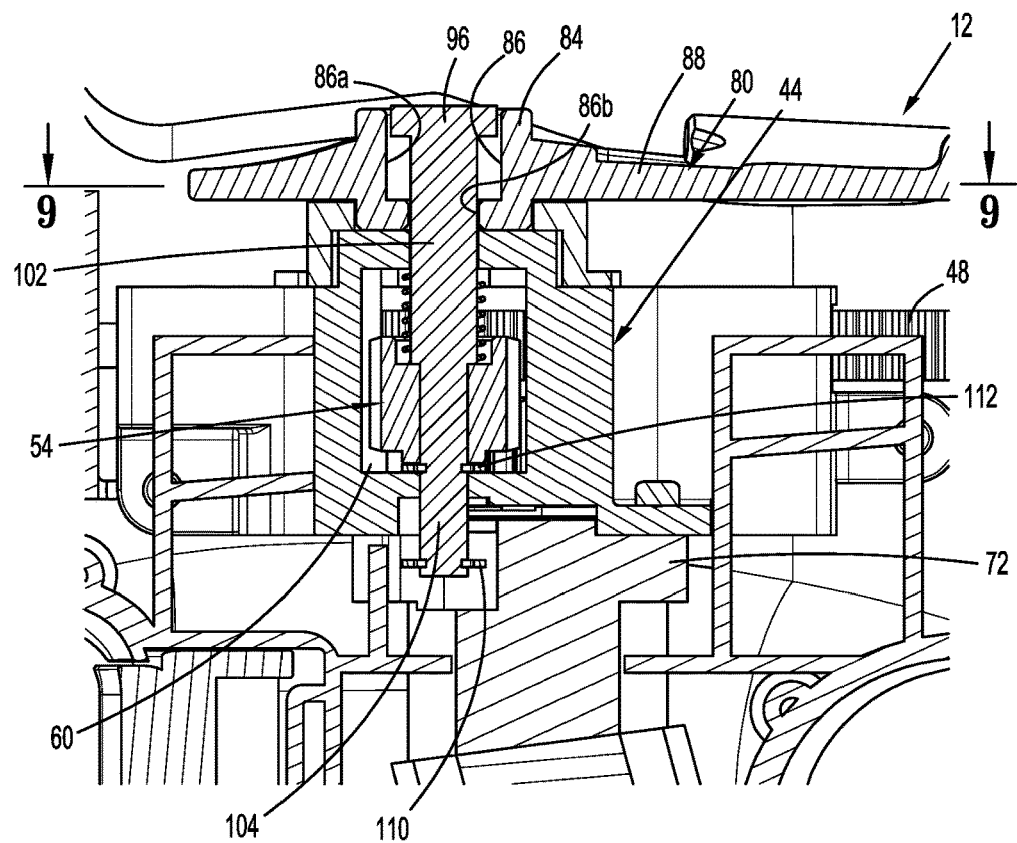
FIG. 8 is a cross-sectional view taken through a portion of the handle assembly shown in FIG. 3 with the stapling device in an unclamped position.
Figure 9:
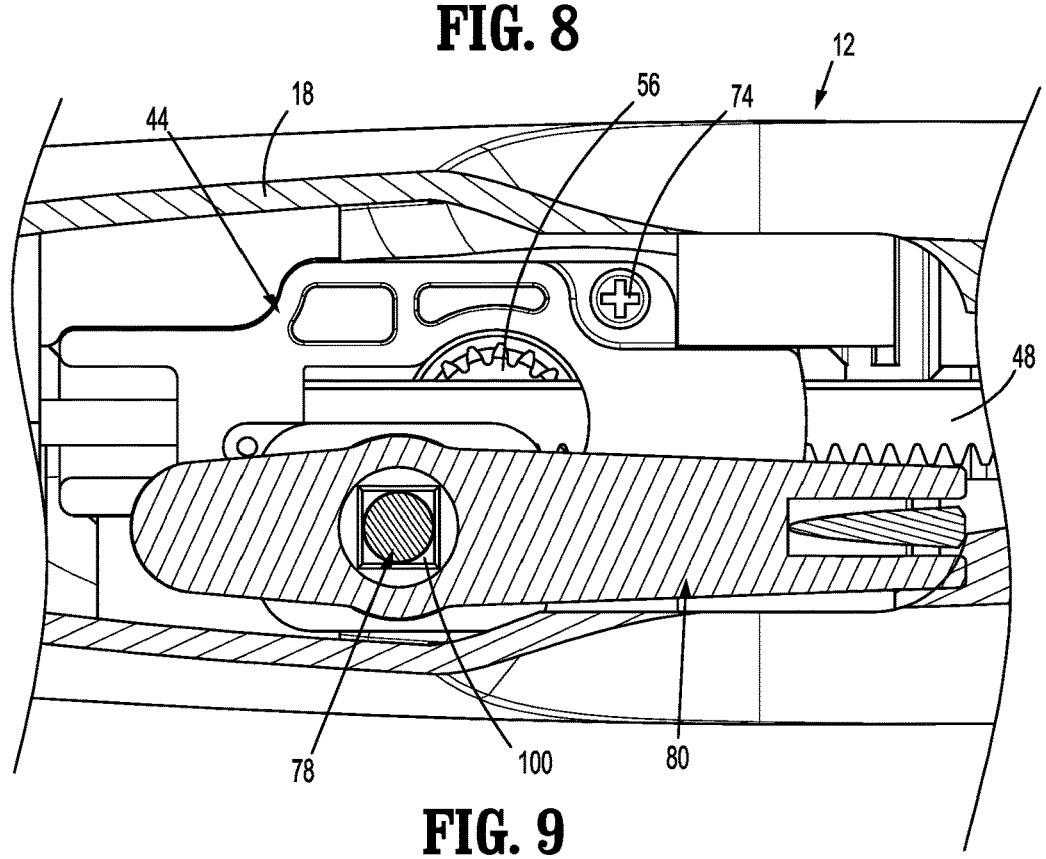
FIG. 9 is a cross-sectional view taken along section line 9-9 of FIG. 8.

FIGS. 7-9 illustrate the handle assembly 12 of the stapling device 10 (FIG. 1) with the stapling device in an unclamped position prior to firing of the stapling device. In this position, the rack 48 is in a retracted position within the channel 64 of the gear casing 44 and the intermediate spur gear 54 is in its lowered position and is engaged with the rack 48 and the drive gear 56.

FIGS. 10 and 11 illustrate the reload assembly 32 when the stapling device 10 is in a fired position. As described above, the reload assembly 32 includes the tool assembly 16 and the proximal body portion 34. In aspects of the disclosure, the tool assembly 16 includes an anvil assembly 150 and a cartridge assembly 152. The cartridge assembly 152 includes a staple cartridge 154 that supports a plurality of staples and pushers (not shown), and an actuation sled 156. The proximal body portion 32 includes a drive assembly 158 that includes a flexible beam 160 and a working end 162. The working end 162 of the drive assembly 158 has an I-beam configuration and is secured to a distal end portion of the flexible beam 160. The flexible beam 160 has a proximal end portion that is releasably coupled to a distal portion of the firing rod 50. When the firing rod 50 is moved from a retracted position to an advanced position, the drive assembly 158 moves from a retracted position to an advanced position to move the working end 162 of the drive assembly 158 through the tool assembly 16 to advance the actuation sled 156 through the tool assembly 16. As the actuation sled 156 moves through the tool assembly 16, the actuation sled 156 engages the pushers (not shown) to eject staples (not shown) from the staple cartridge 154 into the anvil assembly 150. In the fired position, the working end 162 of the drive assembly 158 and the actuation sled 156 are in their advanced positions within the tool assembly and the tool assembly is in the clamped position clamped about tissue (not shown). For a more detailed description of the operation of the drive assembly 158 and its interaction with the tool assembly, see U.S. Pat. No. 8,132,706.

Figure 12:
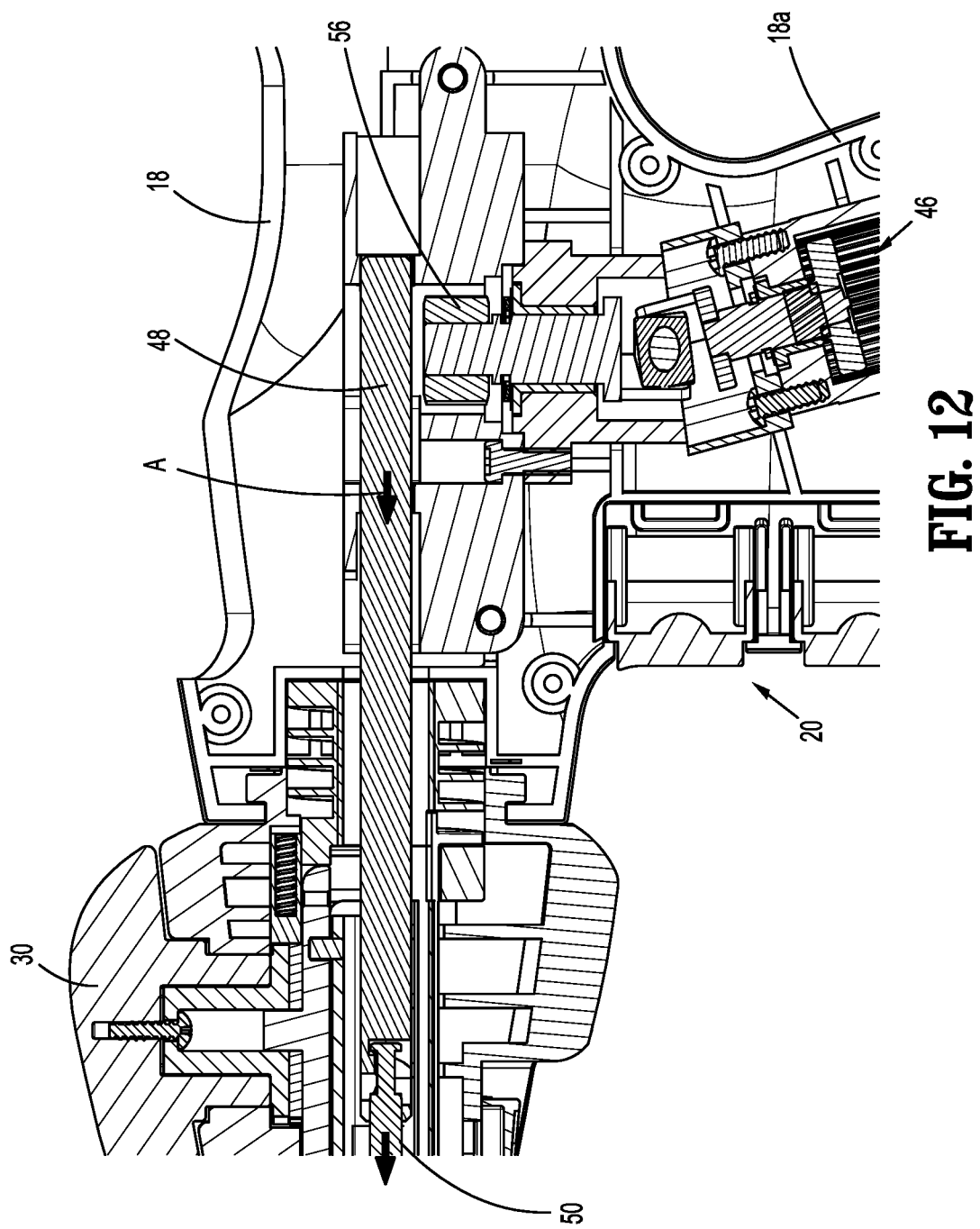
FIG. 12 is a cross-sectional view through a portion of the handle assembly shown in FIG. 3 with the stapling device in the clamped and fired position.

FIG. 12 illustrates the handle assembly 12 of the stapling device 10 (FIG. 1) as the stapling device 10 is fired. When the stapling device 10 is fired, the intermediate spur gear 54 (FIG. 8) is engaged with the rack 48 and with the drive gear 56. When the motor assembly 46 is activated, the drive gear 56 rotates the intermediate spur gear 54 to advance the rack 48 in the direction indicated by arrows "A". The rack 48 is coupled to the firing rod 50 such that advancement of the firing rod 50 advancement of the rack 48 causes advancement of the firing rod 50 in the direction of arrows "A" to advance the drive assembly 158 (FIG. 11) within the tool assembly 16.

Figure 13:
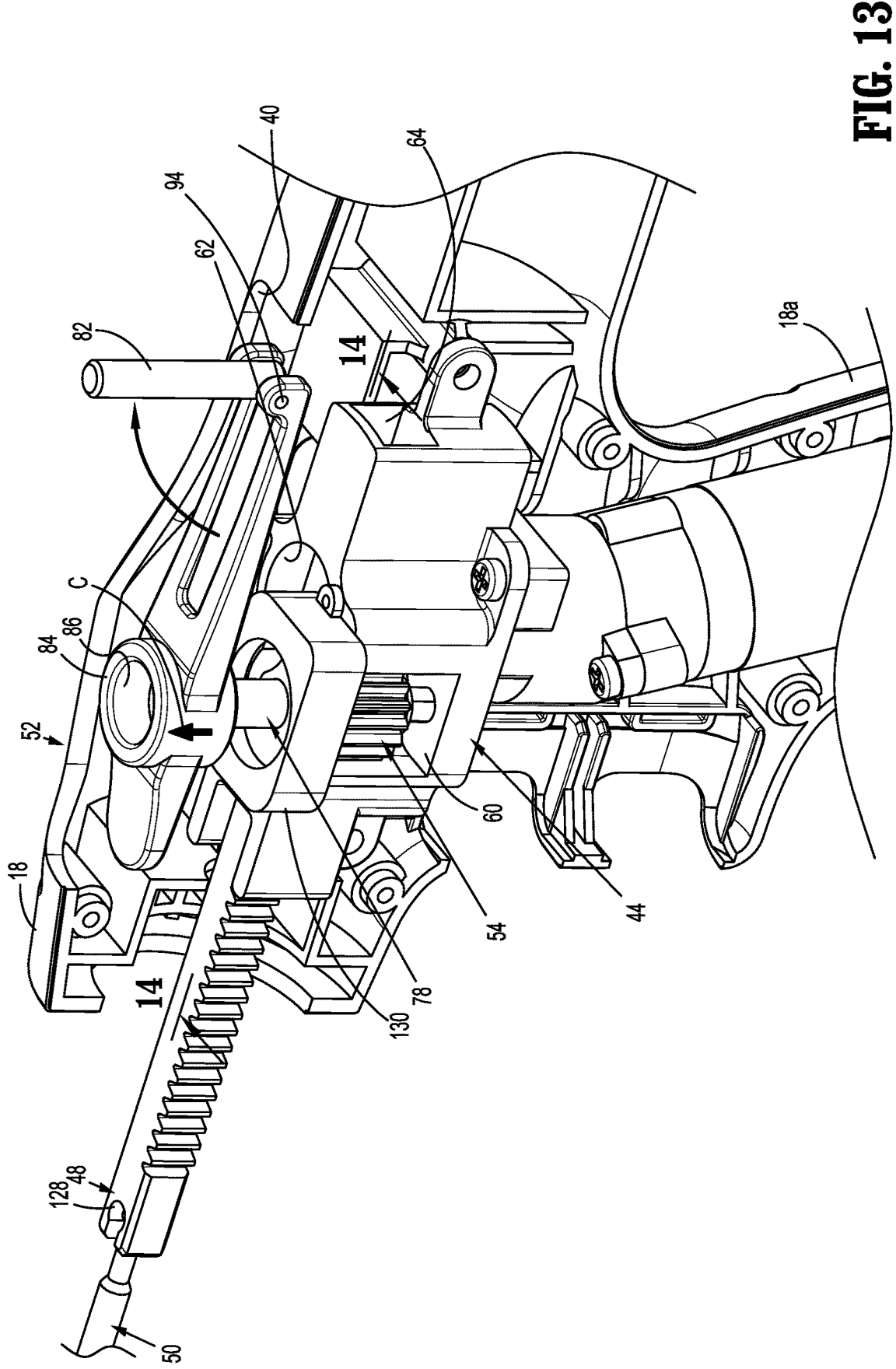
FIG. 13 is a side perspective view of a portion of the handle assembly shown in FIG. 3 as the stapling device is manually retracted from the clamped and fired position.
Figure 14:
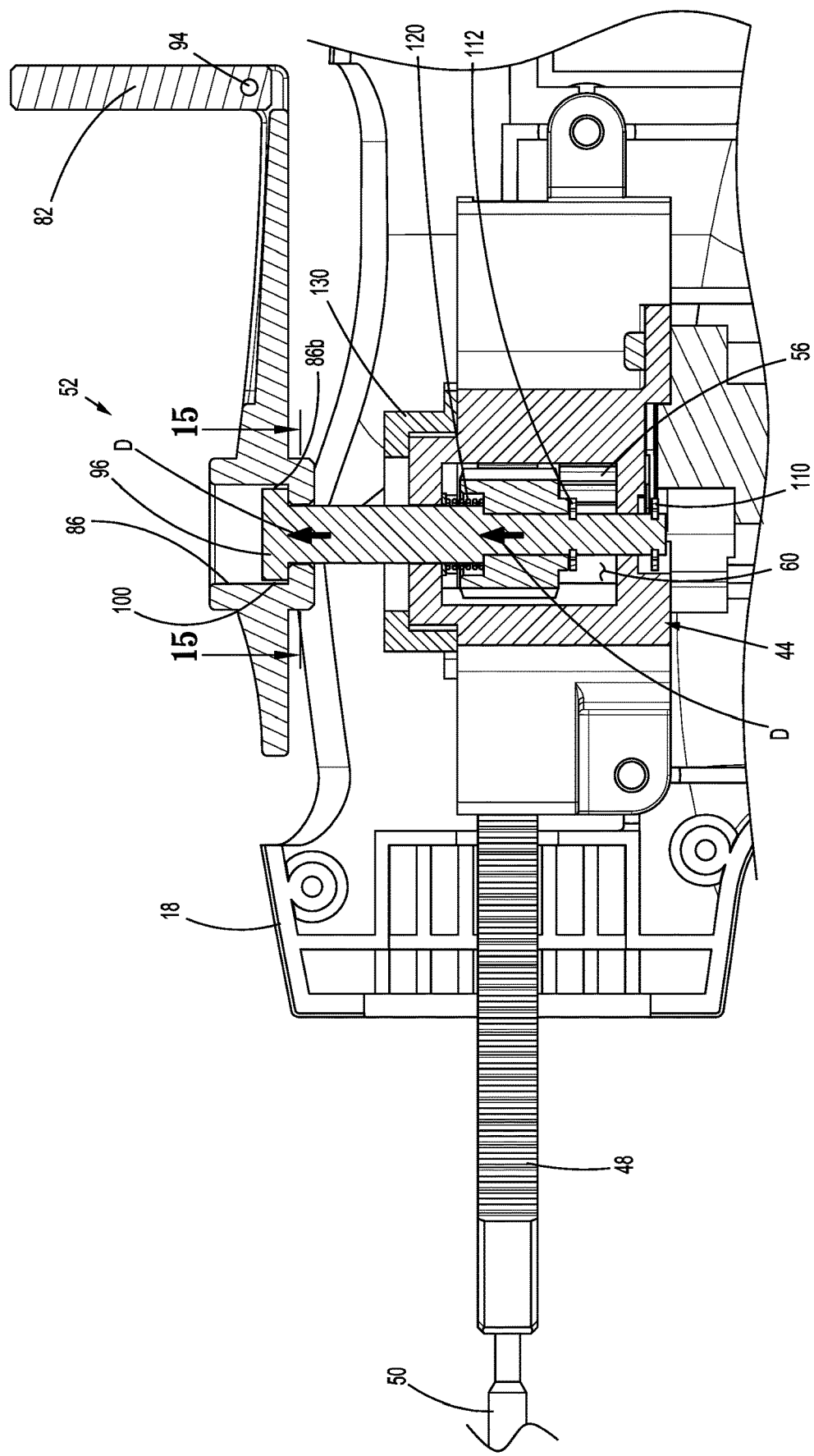
FIG. 14 is a cross-sectional view taken along section line 14-14 of FIG. 13.
Figure 15:
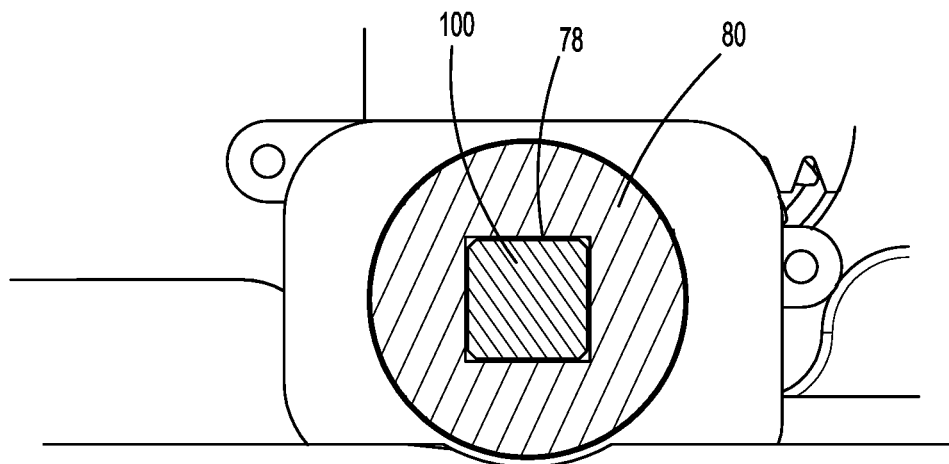
FIG. 15 is a cross-sectional view taken along section line 15-15 of FIG. 14.

FIGS. 13-15 illustrate the manual retract mechanism 52 as it is readied for use. When the stapling device 10 loses power or gets damaged such that the motor assembly 46 cannot retract the drive assembly 158 to release tissue clamped between the anvil and cartridge assemblies 150 and 152 (FIG. 11), the manual retract mechanism 52 can be operated to retract the drive assembly 158 (FIG. 11). In order to access the manual retract mechanism 52, the cover 42 (FIG. 2) must be removed to uncover the upper opening 40 in the housing 18 of the handle assembly 12. Once the cover is removed, the crank lever 80 is pulled upwardly in the direction of arrow "C" in FIG. 13 to move the crank lever 80 from its lowered position to its raised position. As the crank lever 80 is moved towards its raised position, the first rectangular portion 100 of the rotating shaft 78 is received in the rectangular portion 86b of the through bore 86 in the crank lever 80. Once the first rectangular portion 100 of the rotating shaft 78 is received in the rectangular portion 86b of the through bore 86 in the crank lever 80, continued movement of the crank lever 80 in the direction of arrow "C" will lift the rotating shaft 78 and the intermediate spur gear 54 in the direction of arrows "D" in FIG. 14 to their upper positions compressing the biasing member 120. In the upper position, the intermediate spur gear 54 is disengaged from the drive gear 56 and is engaged only with the rack 48. Once the crank lever 80 is in its raised position, the grip member 82 can be pivoted about the pivot member 94 to an operational position.

Figure 16:
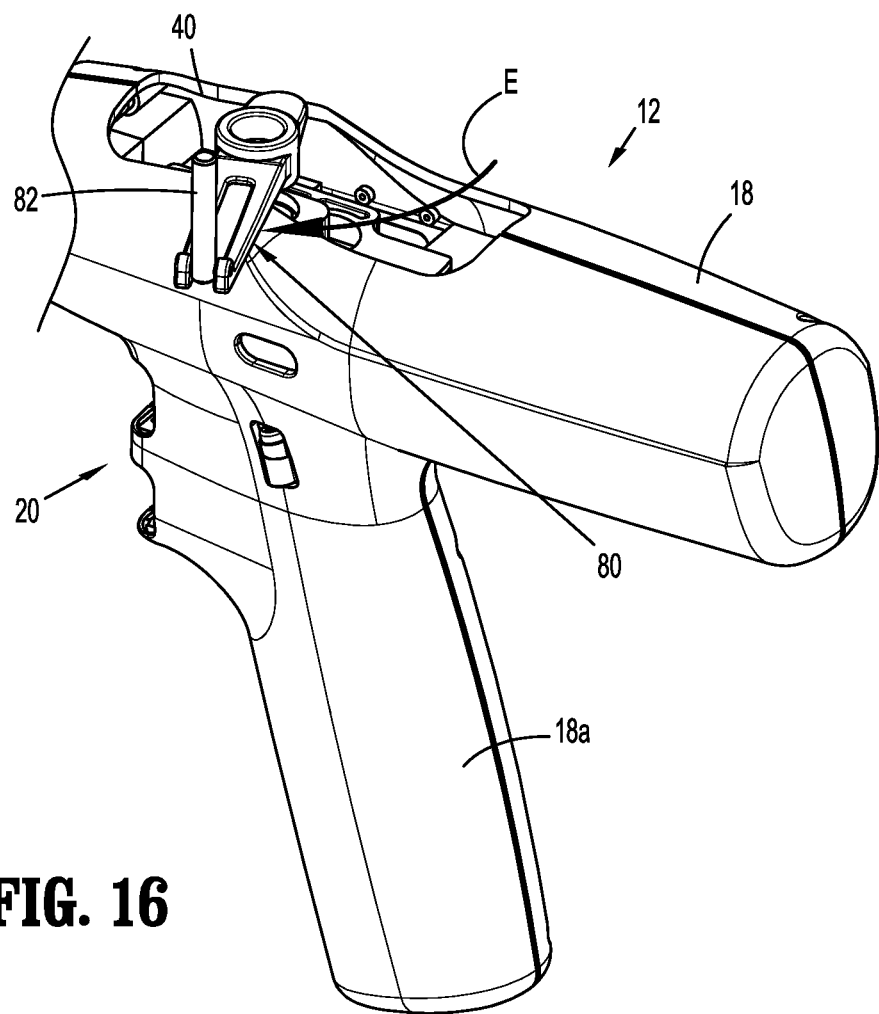
FIG. 16 is a side perspective view of the handle assembly of the stapling device shown in FIG. 1 with the cover of the handle assembly removed as the stapling device is manually retracted.
Figure 17:
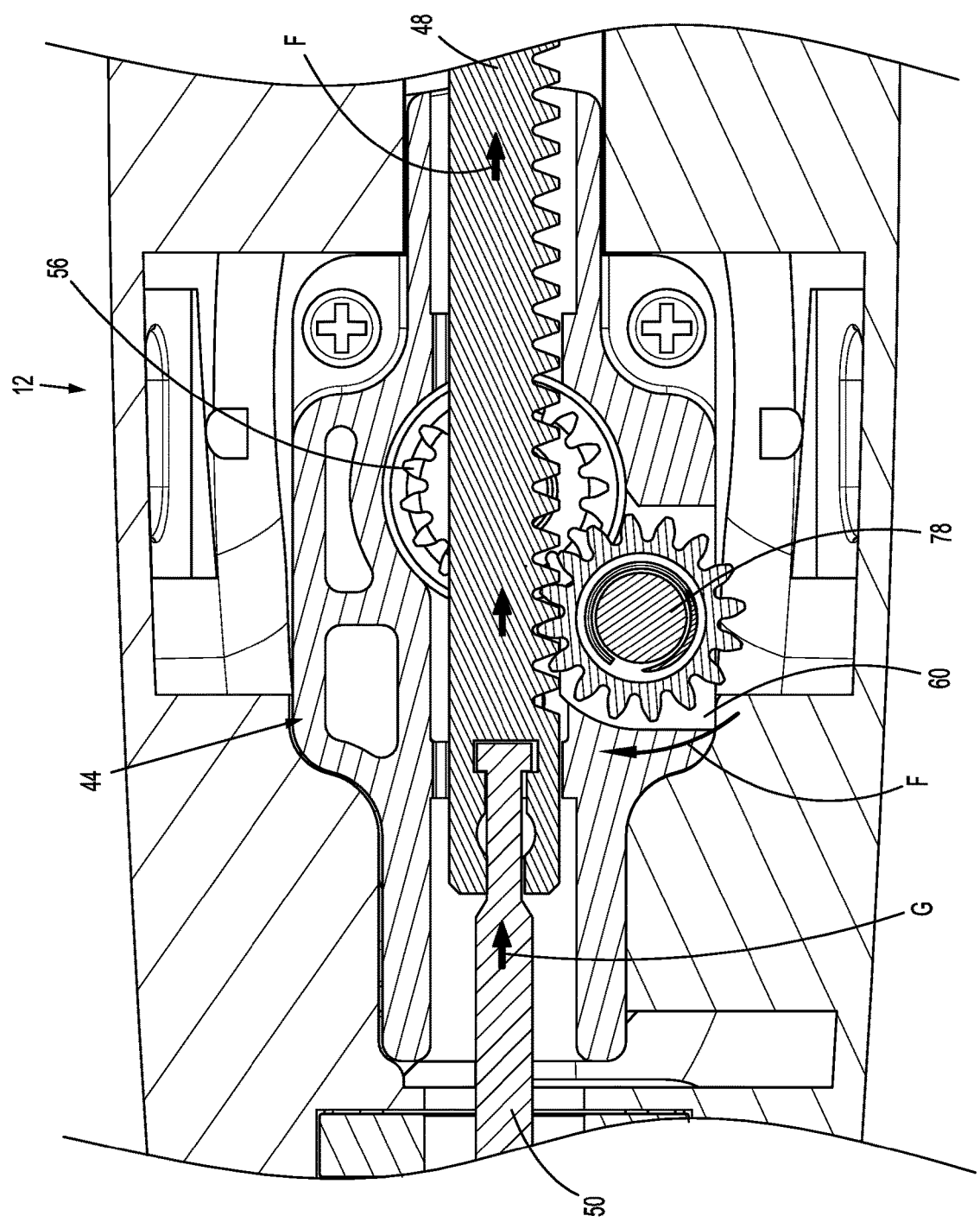
FIG. 17 is a cutaway, cross-sectional view taken through the handle assembly shown in FIG. 16 as the stapling device is manually retracted.

FIGS. 16 and 17 illustrate the manual retract mechanism 52 as it is operated to retract the firing rod 50. Once the crank lever 80 is moved to its raised position, the crank lever 80 can be rotated in the direction indicated by arrow "E" in FIG. in FIG. 16 to rotate the rotating shaft 78 and the intermediate spur gear 54 in the direction indicted by arrow "F" in FIG. 17 to retract the rack 48. More specifically, when the crank lever 80 is rotated, receipt of the first rectangular portion 100 of the rotating shaft 78 in the rectangular portion 86b of the through bore 86 of the crank lever 80 rotatably fixes the crank lever 80 to the rotating shaft 78. Thus, when the crank lever 80 rotates, the rotating shaft also rotates. The intermediate spur gear 54 is rotatably fixed to the rotating shaft 78 via receipt of the second rectangular portion 104 of the rotating shaft 78 in the rectangular bore 54a of the intermediate spur gear 54 such that rotation of the rotating shaft 78 causes rotation of the intermediate spur gear 54. In its upper position, the intermediate spur gear 54 is only engaged with the rack 48, and as such, rotation of the intermediate spur gear 54 causes retract of the rack 48.

FIGS. 19-28 illustrate an alternate version of the handle assembly 12 (FIG. 18) of the stapling device 10 shown generally as handle assembly 312. The handle assembly 312 includes a housing 314 that is substantially similar to housing 18 (FIG. 1) of stapling device 10 and will not be described in further detail herein. The housing 314 defines a cavity 316 that receives the internal components of the handle assembly 312.

Figure 18:
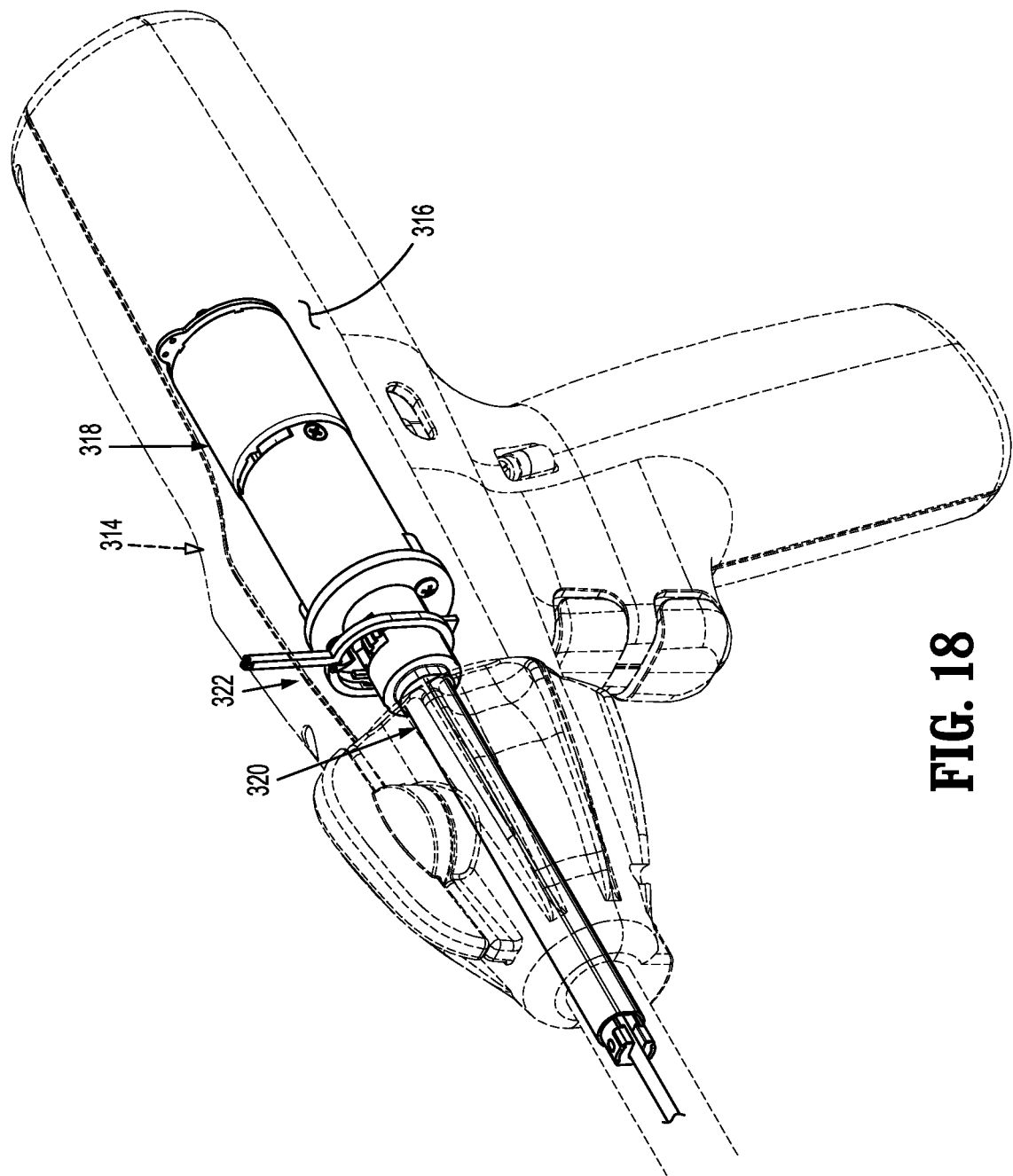
FIG. 18 is an alternate version of the handle assembly of the stapling device shown in FIG. 1 with a housing of the handle assembly shown in phantom.
Figure 19:
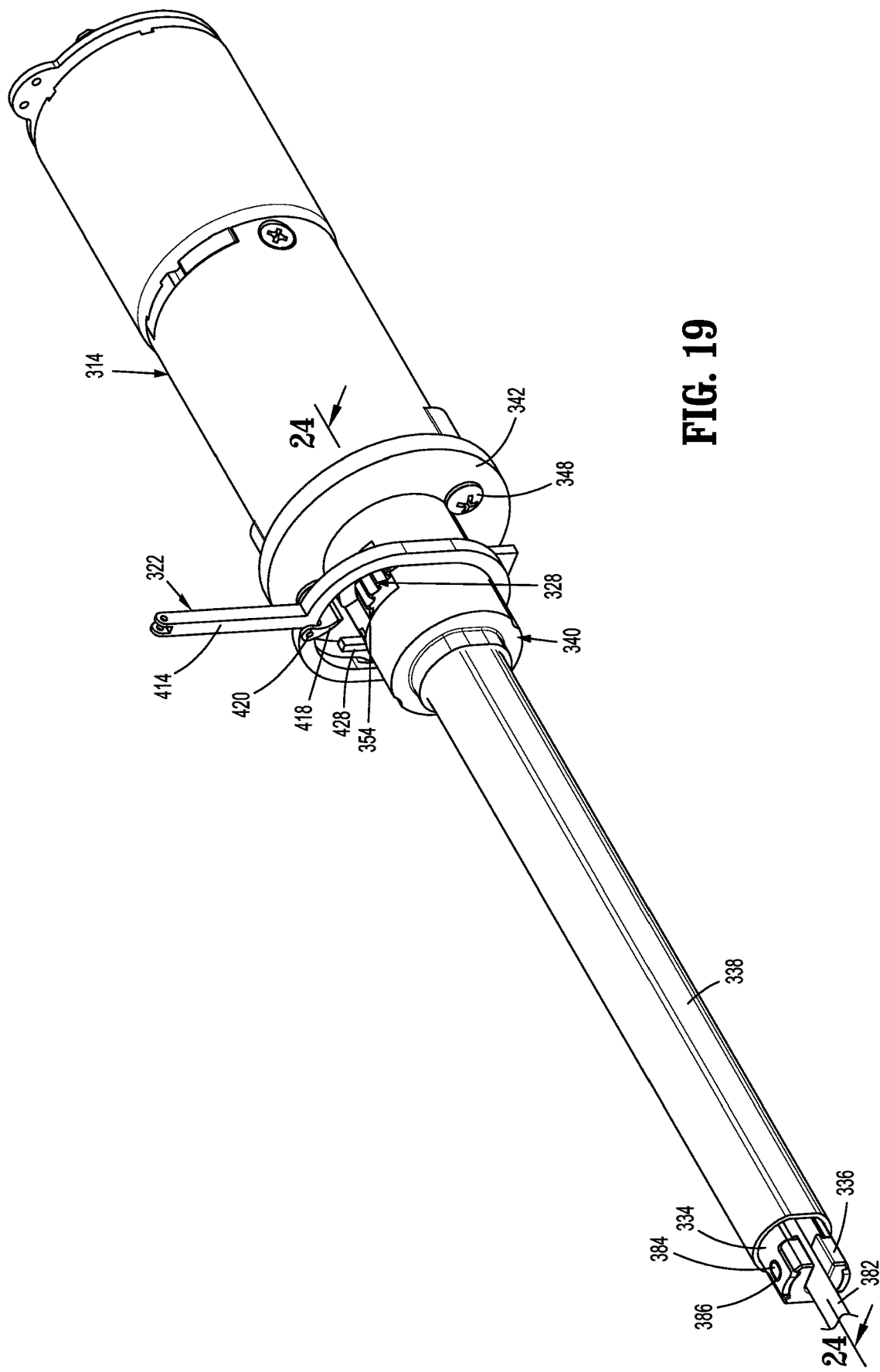
FIG. 19 is an assembled view of the internal components of the handle assembly shown in FIG. 18.
Figure 20:
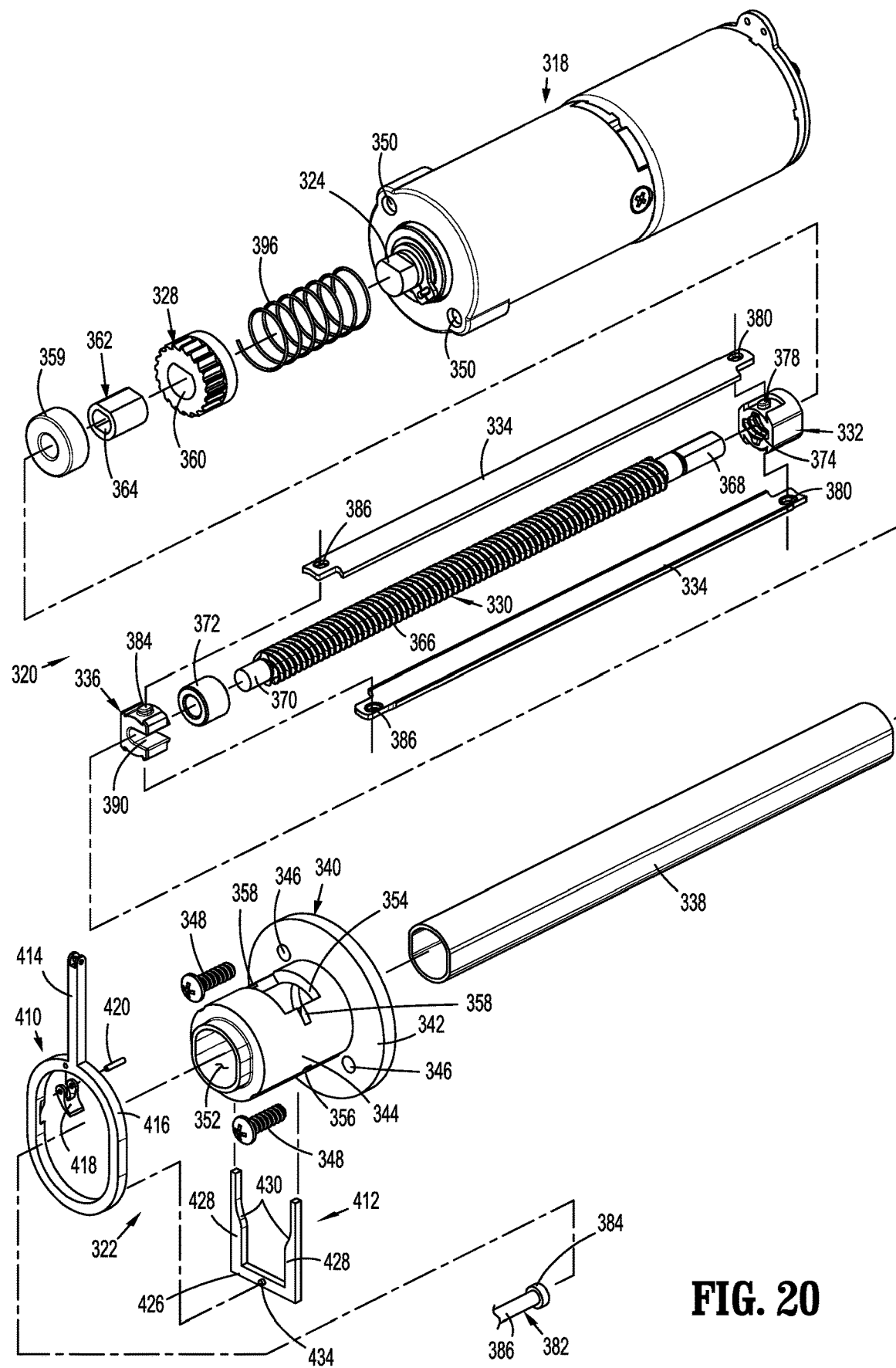
FIG. 20 is an exploded side perspective view of internal components of the handle assembly shown in FIG. 19.

FIGS. 18-20 illustrate the internal components of the handle assembly 312 which includes a motor assembly 318, a drive assembly 320, and a manual retract mechanism 322. The motor assembly 318 is supported within the cavity 316 (FIG. 18) of the housing 314 and includes an output shaft 324 that has a flat surface 324a. In some aspects of the disclosure, the output shaft 324 has a D-shaped configuration although other configurations are envisioned.

The drive assembly 320 is coupled to the output shaft 324 of the motor assembly 318 and includes a one-way spur gear 328, a drive screw 330, a drive nut 332, connecting rods 334, a coupling member 336, a guide tube 338, and a gear casing 340. The gear casing 340 includes a mounting flange 342 and a cylindrical body 344. The mounting flange 342 of the gear casing 340 defines bores 346 that receive screws 348. The screws 348 are received in threaded bores 350 formed in a distal face of the motor assembly 318 to secure the gear casing 340 to the motor assembly 318. The cylindrical body 344 of the gear casing 340 defines a cavity 352 and a window 354 that communicates with the cavity 352. The cylindrical body 344 of the gear casing 340 defines two openings 356 (only one is shown) and two cutouts 358. One of the openings 356 and one of the cutouts 358 is positioned on each side of the window 354 in vertical alignment. The cavity 352 of the cylindrical body 344 of the gear casing 340 receives the one-way spur gear 328. The distal portion of the cylindrical body 344 of the gear casing 340 supports a bearing 359.

The one-way spur gear 328 defines a central through bore 360 that receives a bearing 362. In aspects of the disclosure, the central through bore 360 and the bearing 362 have corresponding non-circular configurations, e.g., D-shaped configurations, such that the bearing 362 is slidably received within the central through bore 360 of the one-way spur gear 328. The corresponding configurations of the one-way spur gear 328 and the bearing 362 rotatably fix the components to each other. The bearing 362 also defines a central through bore 364 that has a non-circular configuration.

The drive screw 330 includes a threaded outer surface 366, a proximal extension 368, and a distal extension 370. The proximal extension 368 of the drive screw 330 extends through the bearing 359 within the gear casing 340 and is received and secured within the central through bore 364 of the bearing 362. The distal extension 370 of the drive screw 330 is received within a bearing 372 that is supported within the housing 314 (FIG. 18) to rotatably support the drive screw 330 within the housing 314.

When the motor assembly 318 is activated to rotate the output shaft 324, rotation of the output shaft 324, when engaged with the one-way spur gear 328, causes corresponding rotation of the one-way spur gear 328. As described above, the one-way spur gear 328 is rotatably fixed to the bearing 362 which is secured to and rotatably fixed to the drive screw 330. As such, rotation of the one-way spur gear 328 causes corresponding rotation of the drive screw 330.

The drive nut 332 includes a threaded bore 374 that receives and is threadably engaged with the threaded outer surface 366 of the drive screw 330. The drive nut 332 is coupled to a proximal portion of the connecting rods 334. In aspects of the disclosure, the drive nut 332 includes protrusions 378 that are received within openings 380 formed in the proximal portions of the connecting rods 334 to connect the drive nut 332 to the connecting rods 334. The connecting rods 334 extend distally from the drive nut 332 and include distal portions that are connected to the coupling member 336. In aspects of the disclosure, the coupling member 336 includes protrusions 384 that are received within openings 386 formed in the distal portions of the connecting rods 334 to connect the coupling member 336 to the connecting rods 334. The drive nut 332 and the connecting rods 334 are received within the guide tube 338.

When the drive screw 330 is rotated, engagement between the outer threaded surface 366 of the drive screw 330 and the inner threaded bore 374 of the drive nut 332 causes the drive nut 332 to translate longitudinally along the drive screw 330 within the guide tube 338. The drive nut 332 is connected to the connecting rods 334 such that longitudinal translation of the drive nut 332 along the drive screw 330 causes the connecting rods 334 to move longitudinally within the guide tube to advance to coupling member 336.

The coupling member 336 is coupled to a firing rod 382 such that longitudinal movement of the coupling member 336 causes longitudinal movement of the firing rod 382. In aspects of the disclosure, the firing rod 382 includes a head portion 384 and an elongate body 386. The head portion 384 has a diameter that is greater than a diameter of the elongate body 386. The coupling member 336 defines a slot 390 that has a width that is greater than the diameter of the elongate body 386 but less than the diameter of the head portion 384. The elongate body 386 of the firing rod 382 is received through the slot 390 in the coupling member 336 to axially fix the firing rod 382 to the coupling member 336 while allowing relative rotation of the firing rod 382 and the coupling member 336.

Figure 26:
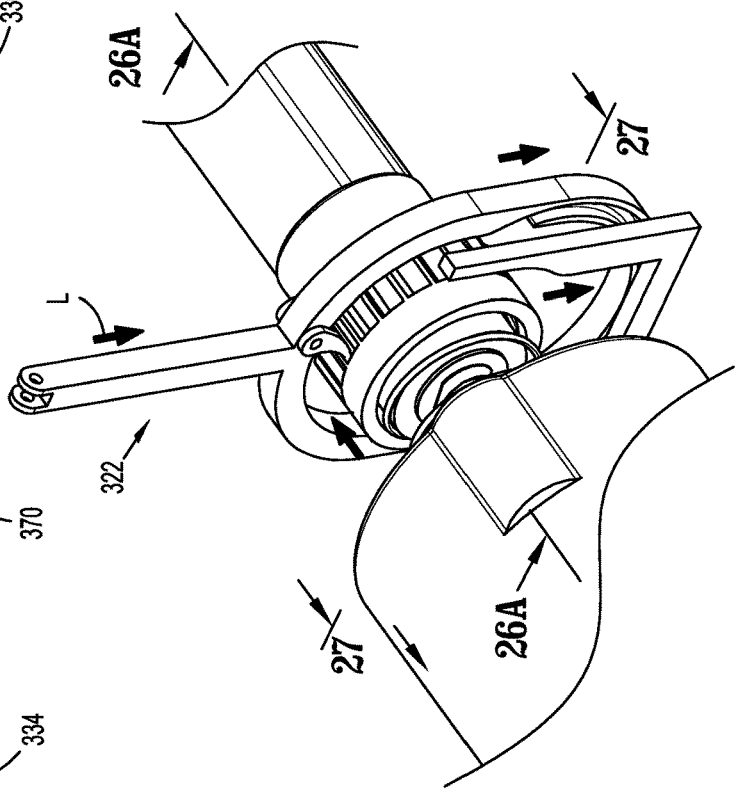
FIG. 26 is a side perspective view from the proximal end of the interface between the motor assembly and the drive assembly of the handle assembly shown in FIG. 19 showing the manual retract mechanism with the locking clip in the unlocked position.
Figure 26A:
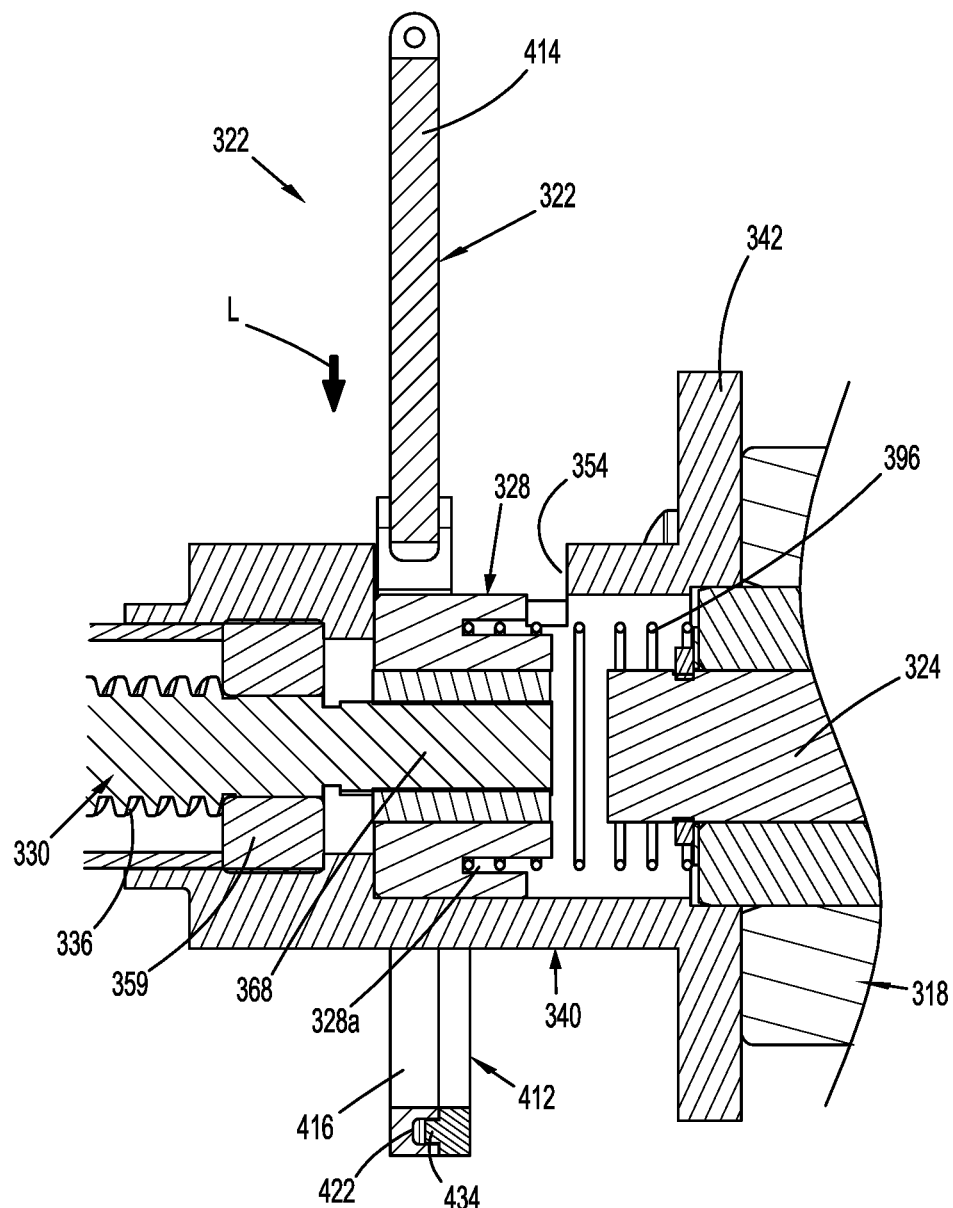
FIG. 26A is a side cross-sectional view taken along section line 26A-26A of FIG. 26 illustrating the manual retract mechanism in the unlocked position.

The one-way spur gear 328 is movably positioned within the cavity 352 of the cylindrical body 344 of the gear casing 340 between a retracted position (FIG. 24) and an advanced position (FIG. 26A). In the advanced position, the one-way spur gear is engaged with the proximal extension 368 of the drive screw 330 and the output shaft 324 of the motor assembly 318 such that rotation of the output shaft 324 of the motor assembly 324 causes rotation of the drive screw 330. In the advanced position, the one-way spur gear 328 is disengaged from the output shaft 324 of the motor assembly 318 but still engaged with the drive screw 330. A biasing member 396, e.g., a coil spring, is positioned between the distal surface of the motor assembly 318 and a proximal surface of the one-way spur gear 328 to urge the one-way spur gear 328 towards the advanced position. In aspects of the disclosure, the proximal surface of the one-way spur gear 328 defines a recess 328a (FIG. 26A) that receives the biasing member 396.

Figure 21:
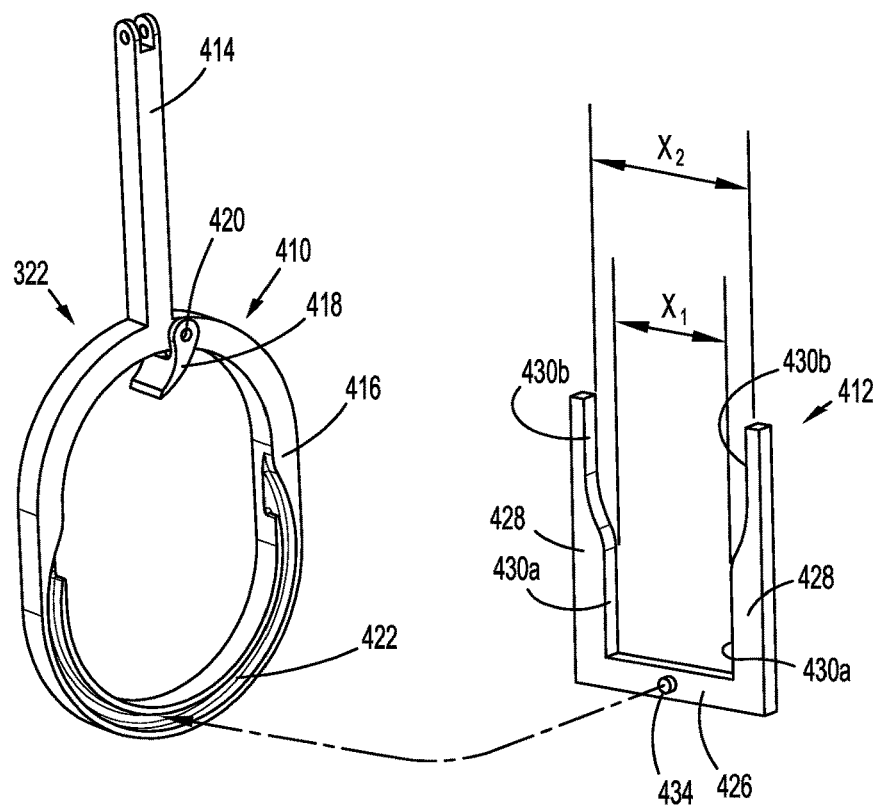
FIG. 21 is a side perspective view of a pawl assembly and locking clip of the handle assembly shown in FIG. 19.

FIGS. 20 and 21 illustrate the manual retract mechanism 322 includes a pawl assembly 410 and a locking clip 412.

The pawl assembly 410 includes a handle 414 and a body portion 416. In aspects of the disclosure, the body portion has an oval or annular configuration and supports a ratcheting pawl 418 that is pivotably secured to an upper portion of the body portion 416 by a pivot member 420. The ratcheting pawl 418 extends downwardly into a circular opening defined by the body portion 416. The body portion 416 is received about the gear casing 340 with the ratcheting pawl 418 positioned over the window 354 in the gear casing 340 above the one-way spur gear 328. A lower portion of the body portion 416 defines a circular slot 422.

The locking clip 412 has a rectangular shape and includes a base portion 426 and spaced legs 428 that extend upwardly from the base portion 426. Each of the legs 428 of the locking clip 412 includes a stepped inner surface 430 that includes a first surface 430a and a second surface 430b. The first surfaces 430a of the legs 428 define a first width $X_1$ and the second surfaces 430b define a second width $X_2$ that is greater than the first width $X_2$. Each of the legs 428 is received through one of the openings 356 and cutouts 358 of the gear casing 340 such that the stepped inner surfaces 430 of the legs 428 of the locking clip 412 are positioned within the cavity 352 of the gear casing 340. The locking clip 322 is movable from a first position (FIG. 23) in which the first surfaces 430a of the legs 428 of the locking clip 322 are aligned with the one-way spur gear 328 and a second position in which the second surfaces 430b of the legs 428 of the locking clip 322 are spaced from the one-way spur gear 328. The width $X_1$ between the first surfaces 430a of the legs 428 of the locking clip 322 is such to prevent movement of the one-way spur gear 322 to its advanced position, whereas the width $X_2$ between the second surfaces 430b of the legs 428 of the locking clip 322 allows movement of the one-way spur gear 322 to the advanced position.

The base portion 426 of the locking clip 322 includes a protrusion 434 that is received within the circular slot 422 in the body portion 416 of the pawl assembly 410. Receipt of the protrusion 434 couples the pawl assembly 410 to the locking clip 322 to retain the pawl assembly 410 in a stable position about the gear casing 340. In aspects of the disclosure, the protrusion 434 has an enlarged head and the circular slot includes overhanging ledges that retain the enlarged head of the protrusion 434 within the circular slot 422. The protrusion 434 is configured to slide within the circular slot 422 as described in further detail below.

Figure 22:
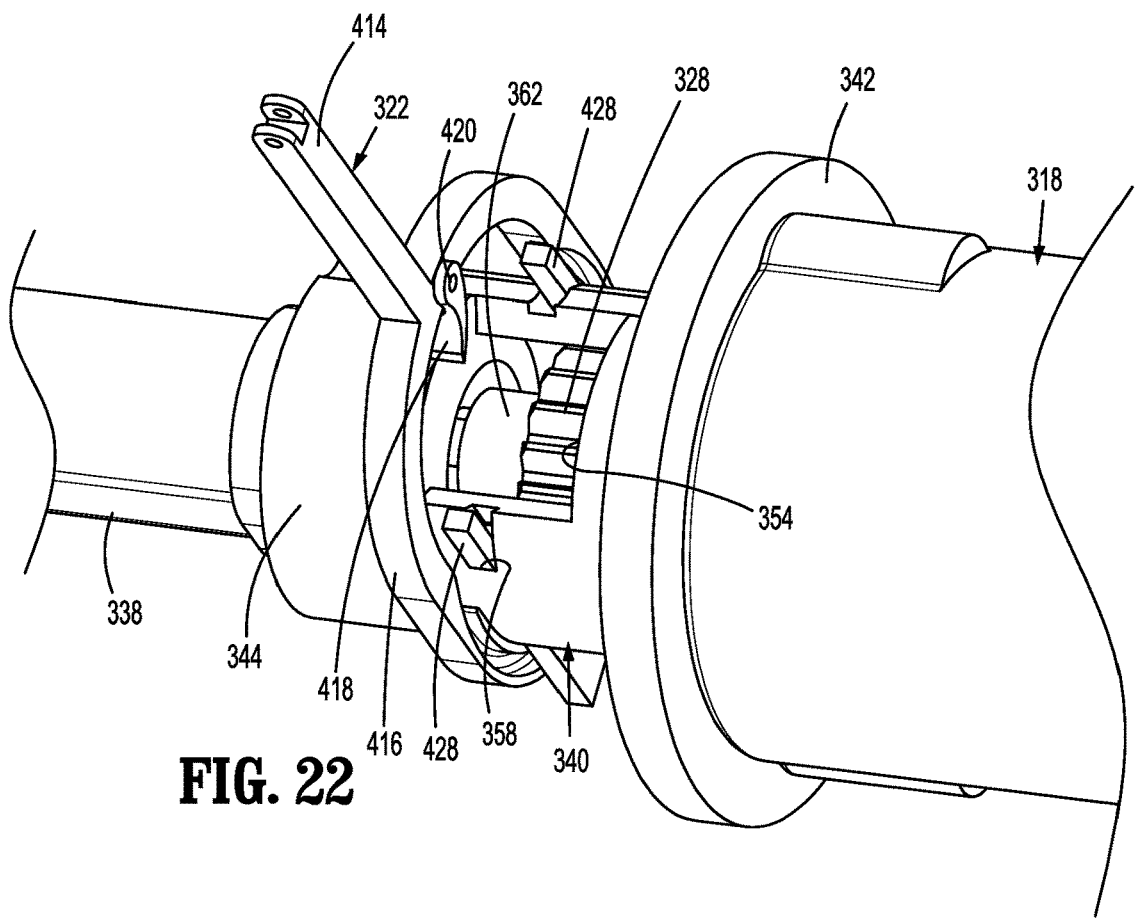
FIG. 22 is a side perspective view from the proximal end of an interface between a motor assembly and a drive assembly of the handle assembly shown in FIG. 19 showing a manual retract mechanism with the locking clip in the locked position.
Figure 23:
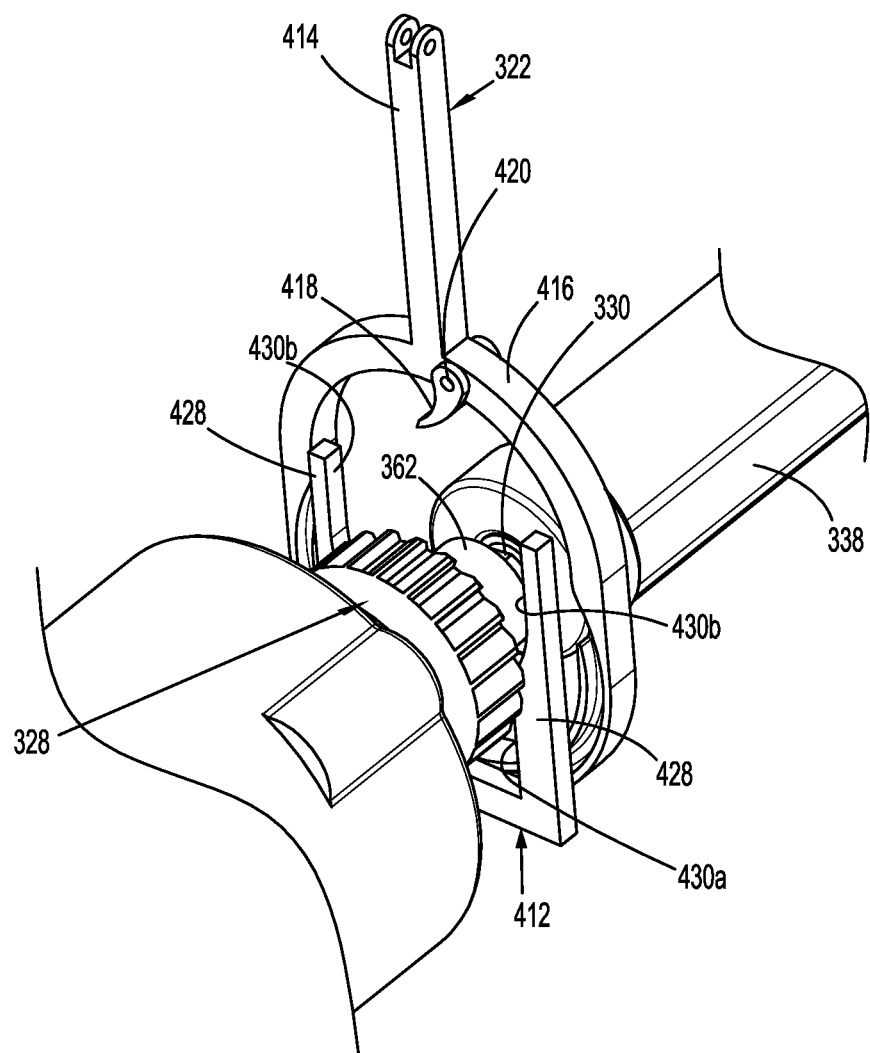
FIG. 23 is a side perspective view from the distal end of the interface between the motor assembly and the drive assembly of the handle assembly shown in FIG. 20 with a gear casing removed showing the manual retract mechanism with the locking clip in the locked position.
Figure 24:
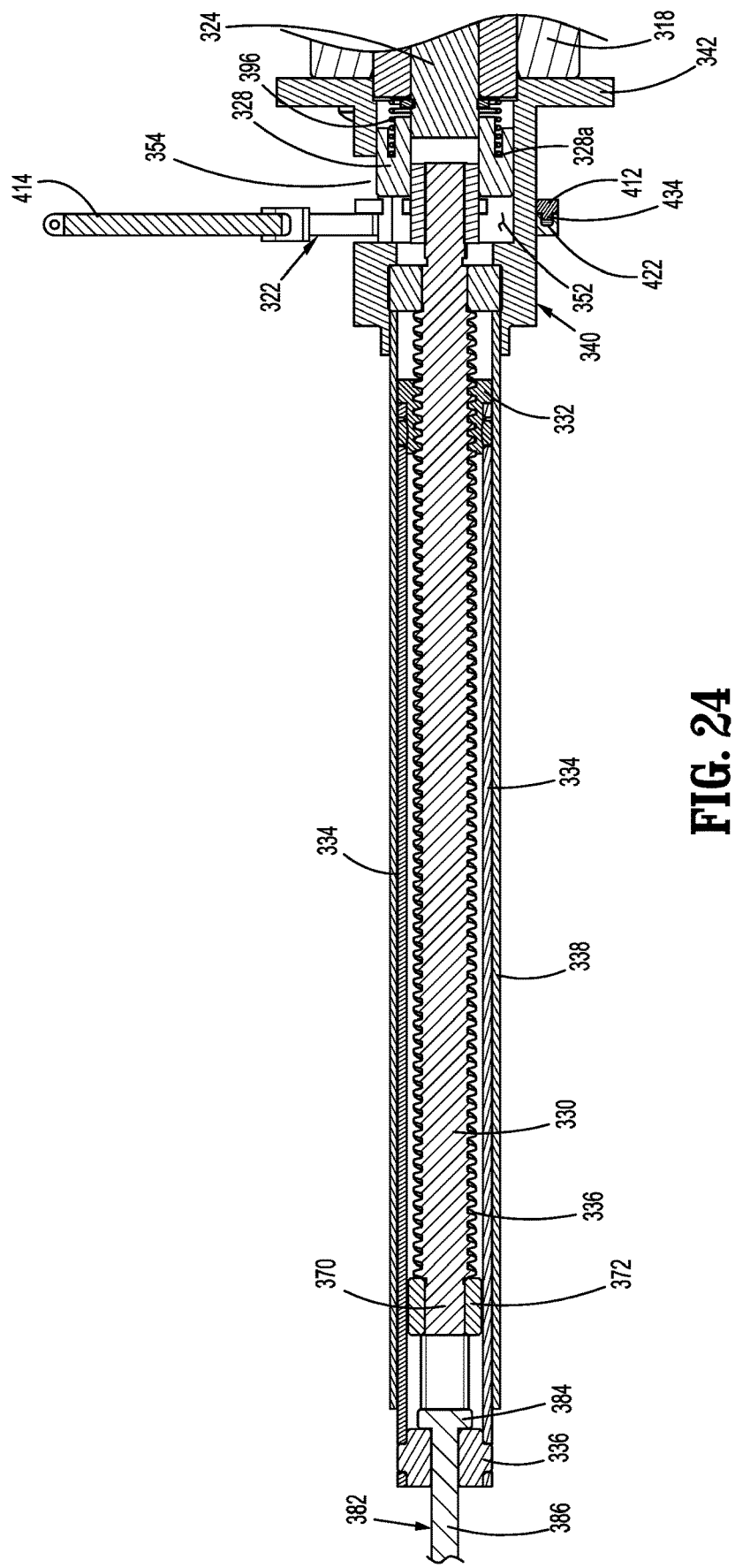
FIG. 24 is a cross-sectional view taken along section line 24-24 of FIG. 19.

FIGS. 22-24 illustrate the handle assembly 12 (FIG. 18) in a pre-fired position with the pawl assembly 322 positioned about the gear casing 340 and the ratcheting pawl 418 positioned above the window 354 in the gear casing 340. When the handle assembly 12 is assembled, the one-way spur gear 328 is pressed proximally towards the motor assembly 318 to compress the biasing member 396 and position the one-way spur gear 328 in its retracted position. After the one-way spur gear 328 is in its retracted position, the legs 428 of the locking clip 412 are inserted from a side of the gear casing 340 opposite to the ratcheting pawl 418 into the openings 356 and cutouts 358 formed in the gear casing 340 to its first position. In the first position of the locking clip 412, the first surfaces 430a of the legs 428 of the locking clip 412 engage a distal face of the one-way spur gear 328 to retain the one-way spur gear 328 in its retracted position against the urging of the biasing member 396. In its retracted position, the one-way spur gear 328 is engaged with both the output shaft 324 of the motor assembly 318 and the one-way spur gear 328. When the locking clip 412 is in its first position, the protrusion 434 on the locking clip 412 is pressed into the circular slot 422 on the body portion 416 of the pawl assembly 322 to couple the pawl assembly 322 to the locking clip 412 (FIG. 24).

In the pre-fired position of the handle assembly 12 (FIG. 18), the drive nut 322 is positioned near the proximal end of the drive screw 330 and the coupling member 336 is positioned adjacent the distal end of the guide tube 338 such that the connecting rods 334 are in retracted positions and the firing rod 382 is in its retracted position.

Figure 25:
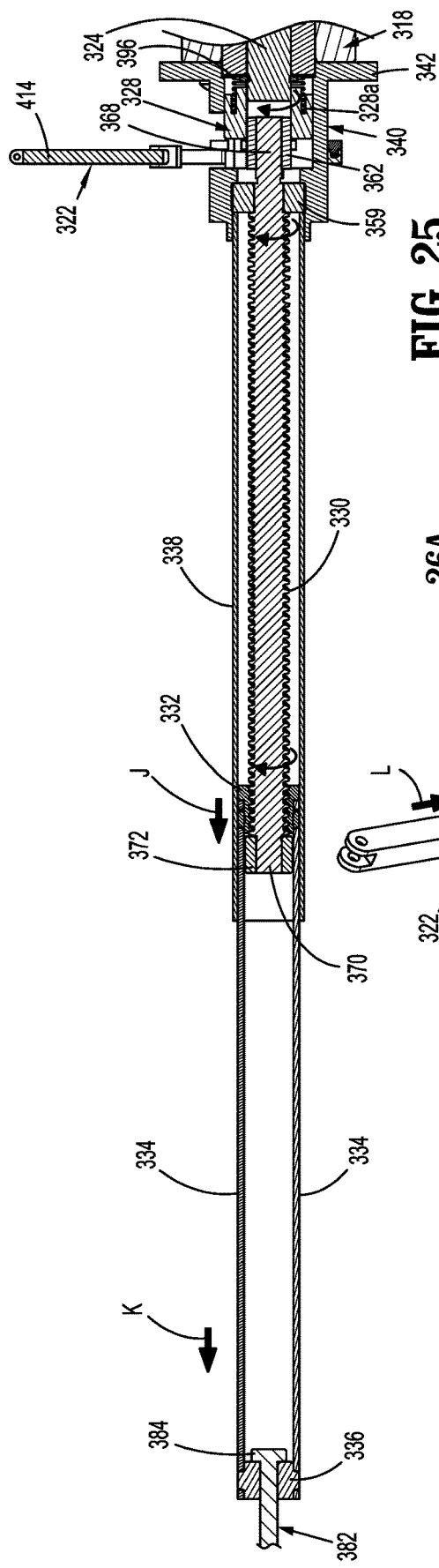
FIG. 25 is a side cross-sectional view of the drive assembly of the handle assembly of the stapling device shown in FIG. 24 in the fired position.

FIG. 25 illustrates the handle assembly 12 (FIG. 1) in a fired position. When the stapling device 10 (FIG. 1) is fired by pressing the actuation buttons 20 (FIG. 1), the motor assembly 318 is activated to rotate the output shaft 324. Rotation of the output shaft 324 causes corresponding rotation of the one-way spur gear 328 and the drive screw 330 to advance the drive nut 322 along the drive screw 330 in the direction of arrow "J". As the drive screw 330 advances the drive nut 322, the drive nut 322 advances the connecting rods 334 to advance the firing rod 382 in the direction of arrow "K" and actuate the tool assembly 16 (FIG. 1) as described above regarding stapling device 10 (FIG. 1).

When the tool assembly 16 is in the clamped and fired position (FIG. 11) and the powered stapling device 10 (FIG. 1) becomes inoperable and cannot be unclamped using the motor assembly 318, the manual retract mechanism 322 allows the tool assembly to be manually unclamped. FIGS. 26-28 illustrate operation of the manual retract mechanism 322. In order to operate the manual retract mechanism 322, the pawl assembly 322 is pressed downwardly in the direction of arrows "L" in FIGS. 26-27. When the pawl assembly 322 is pressed downwardly, the locking clip 412, which is coupled to the pawl assembly 322 by the protrusion 434, is moved from its first position to its second position. In its second position, the locking clip 412 disengages from the one-way spur gear 328 such that the biasing member 396 moves the one-way spur gear 328 from its retracted position to its advanced position. In its advanced position, the one-way spur gear 328 is disengaged from the output shaft 324 of the motor assembly 318. When the pawl assembly 322 is pressed downwardly, the ratcheting pawl 418 moves through the window 354 of the gear housing 340 into engagement with the one-way spur gear 328.

After the one-way spur gear 328 is in its advanced position, the handle 414 of the pawl assembly 322 can be rotated in the direction of arrow "M" in FIG. 28 to rotate the one-way spur gear 328 and the drive screw 330 to retract the firing rod 382. As the pawl assembly 322 is rotated, the protrusion 434 moves within the circular slot 422 of the pawl assembly 322.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A powered handle assembly for a surgical device comprising:
   a housing defining a cavity;
   a gear casing supported within the cavity of the housing, the gear casing defining a channel, a motor assembly including an output shaft and a drive gear secured to the output shaft, the motor assembly secured to the gear casing, and the drive gear being positioned within the cavity of the gear casing;

a drive screw supported within the housing, the drive screw rotatable in response to activation of the motor assembly;

a drive nut supported on and movable along the drive screw, the drive nut movable between retracted and advanced positions;

a connecting rod coupled to the drive nut; and a spur gear movable within the channel of the gear casing from a first position in which the spur gear is engaged with the output shaft and the drive screw to a second position in which the spur gear is disengaged from the output shaft and engaged with the drive screw.

2. The powered handle assembly of claim 1, further including a biasing member positioned to urge the spur gear to the second position.

3. The powered handle assembly of claim 2, further including a locking clip, the locking clip movable from a first position retaining the spur gear in its first position to a second position allowing movement of the spur gear from its first position to its second position.

4. The powered handle assembly of claim 3, further including a pawl assembly including a body portion and a ratcheting pawl coupled to the body portion.

5. The powered handle assembly of claim 4, wherein the gear casing defines a window and the body portion of the pawl assembly is positioned about the gear casing adjacent the window, the pawl assembly being movable from a first position in which the ratcheting pawl is spaced from the spur gear to a second position in which the ratcheting pawl is engaged with the spur gear.

6. The powered handle assembly of claim 4, wherein the pawl assembly is coupled to the locking clip such that movement of the pawl assembly from its first position to its second position moves the locking clip from its first position to its second position.

7. The powered handle assembly of claim 1, wherein the gear casing defines spaced openings and the locking clip includes legs that are received within the openings.

8. The powered handle assembly of claim 1, wherein the connecting rod includes a proximal portion coupled to the drive nut and a distal portion coupled to a coupling member.

9. The powered handle assembly of claim 8, wherein the coupling member is adapted to engage a firing rod of the surgical device.

10. A stapling device comprising:
a powered handle assembly including:
  a housing defining a cavity;
  a gear casing supported within the cavity of the housing, the gear casing defining a channel;
  a motor assembly including an output shaft and a drive gear secured to the output shaft, the motor assembly secured to the gear casing, and the drive gear being positioned within the cavity of the gear casing;
  a drive screw supported within the housing, the drive screw rotatable in response to activation of the motor assembly;
  a drive nut supported on and movable along the drive screw, the drive nut movable between retracted and advanced positions;
  a connecting rod coupled to the drive nut; and
  a spur gear movable within the channel of the gear casing from a first position in which the spur gear is engaged with the output shaft and the drive screw to a second position in which the spur gear is disengaged from the output shaft and engaged with the drive screw;

an adapter assembly having a proximal portion and a distal portion, the proximal portion coupled to the handle assembly, the adapter assembly including a firing rod that is coupled to the drive nut and movable between retracted and advanced positions in response to movement of the drive nut between its retracted and advanced positions; and a tool assembly supported on the distal portion of the adapter assembly.

11. The stapling device of claim 10, further including a biasing member positioned to urge the spur gear to the second position.

12. The stapling device of claim 11, further including a locking clip, the locking clip movable from a first position retaining the spur gear in its first position to a second position allowing movement of the spur gear from its first position to its second position.

13. The stapling device of claim 12, further including a pawl assembly including an annular body portion and a ratcheting pawl coupled to the body portion.

14. The stapling device of claim 13, wherein the gear casing defines a window and the annular body portion of the pawl assembly is positioned about the gear casing adjacent the window, the pawl assembly being movable from a first position in which the ratcheting pawl is spaced from the spur gear to a second position in which the ratcheting pawl is engaged with the spur gear.

15. The powered handle assembly of claim 1, wherein the gear casing defines spaced openings and the locking clip includes legs that are received within the openings.

16. The stapling device of claim 10, wherein the connecting rod includes a proximal portion coupled to the drive nut and a distal portion coupled to a coupling member.

17. The stapling device of claim 16, wherein the connecting rod includes first and second connecting rods.

18. The stapling device of claim 17, wherein the pawl assembly is coupled to the locking clip such that movement of the pawl assembly from its first position to its second position moves the locking clip from its first position to its second position.

19. A powered handle assembly for a surgical device comprising:
a housing defining a cavity;
a motor assembly including an output shaft and a drive gear secured to the output shaft, the motor assembly positioned within the housing, and the drive gear being positioned within the cavity of the gear casing;
a drive screw supported within the housing, the drive screw rotatable in response to activation of the motor assembly;
a drive nut supported on and movable along the drive screw, the drive nut movable between retracted and advanced positions;
a connecting rod coupled to the drive nut;
a spur gear movable within the cavity of the housing from a first position in which the spur gear is engaged with the output shaft and the drive screw to a second position in which the spur gear is disengaged from the output shaft and engaged with the drive screw;
a locking clip movable from a first position retaining the spur gear in its first position to a second position allowing movement of the spur gear from its first position to its second position; and a pawl assembly including an annular body portion and a ratcheting pawl coupled to the body portion.

20. The powered handle assembly of claim 19, wherein the gear casing defines a window and the annular body portion of the pawl assembly is positioned about the gear casing adjacent the window, the pawl assembly being movable from a first position in which the ratcheting pawl is spaced from the spur gear to a second position in which the ratcheting pawl is engaged with the spur gear.

\* \* \* \* \*